(12) United States Patent
Leone-Bay et al.

(10) Patent No.: US 7,951,971 B1
(45) Date of Patent: *May 31, 2011

(54) PHENOXY CARBOXYLIC ACID COMPOUNDS AND COMPOSITIONS FOR DELIVERING ACTIVE AGENTS

(75) Inventors: Andrea Leone-Bay, Ridgefield, CT (US); Kelly Kraft, Hopewell Junction, NY (US); Destardi Moye-Sherman, Newburgh, NY (US); David Gscheidner, Thornwood, NY (US); Maria Aurora P. Boyd, Garrison, NY (US); Puchun Liu, Chappaqua, NY (US); Pingwah Tang, Elmsford, NY (US); Jun Liao, Yorktown Heights, NY (US); John Smart, Katonah, NY (US); John J. Freeman, Jr., New Fairfield, CT (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 258 days.

This patent is subject to a terminal disclaimer.

(21) Appl. No.: 12/139,276

(22) Filed: Jun. 13, 2008

Related U.S. Application Data

(63) Continuation of application No. 11/458,331, filed on Jul. 18, 2006, which is a continuation of application No. 10/129,467, filed as application No. PCT/US00/30662 on Nov. 6, 2000, now Pat. No. 7,129,274.

(60) Provisional application No. 60/163,806, filed on Nov. 5, 1999, provisional application No. 60/231,836, filed on Sep. 6, 2000, provisional application No. 60/237,233, filed on Oct. 2, 2000.

(51) Int. Cl.
C07C 65/30 (2006.01)
(52) U.S. Cl. ........................................................ 562/459
(58) Field of Classification Search .................. None
See application file for complete search history.

(56) References Cited

U.S. PATENT DOCUMENTS

| | | | |
|---|---|---|---|
| 2,375,138 A | 5/1945 | Salvin et al. |
| 3,369,025 A | 2/1968 | Bolhofer |
| 3,452,081 A | 6/1969 | Sprague et al. |
| 3,674,836 A | 7/1972 | Creger |
| 3,707,566 A | 12/1972 | Creger et al. |
| 3,759,986 A | 9/1973 | Creger et al. |
| 3,795,739 A | 3/1974 | Birkmayer et al. |
| 3,939,253 A | 2/1976 | Bodor et al. |
| 4,013,451 A | 3/1977 | Poignant et al. |
| 4,035,507 A | 7/1977 | Bodor et al. |
| 4,060,619 A | 11/1977 | Philipp et al. |
| 4,061,466 A | 12/1977 | Sjoholm et al. |
| 4,147,767 A | 4/1979 | Yapel, Jr. |
| 4,238,506 A | 12/1980 | Stach et al. |
| 4,239,754 A | 12/1980 | Sache et al. |
| 4,393,192 A | 7/1983 | Curatolo et al. |
| 4,410,537 A | 10/1983 | Kneen et al. |
| 4,412,041 A | 10/1983 | Kitahara et al. |
| 4,442,090 A | 4/1984 | Kakeya et al. |
| 4,462,991 A | 7/1984 | Higuchi et al. |
| 4,464,363 A | 8/1984 | Higuchi et al. |
| 4,470,980 A | 9/1984 | Higuchi et al. |
| 4,499,299 A | 2/1985 | Bernstein et al. |
| 4,654,327 A | 3/1987 | Teng |
| 4,656,161 A | 4/1987 | Herr et al. |
| 4,692,433 A | 9/1987 | Hostetler et al. |
| 4,757,066 A | 7/1988 | Shiokari et al. |
| 4,800,162 A | 1/1989 | Matson |
| 4,835,312 A | 5/1989 | Itoh et al. |
| 4,873,087 A | 10/1989 | Morishita et al. |
| 4,878,942 A | 11/1989 | Motegi et al. |
| 4,900,730 A | 2/1990 | Miyauchi et al. |
| 4,927,928 A | 5/1990 | Shroot et al. |
| 5,066,487 A | 11/1991 | Morelle et al. |
| 5,352,461 A | 10/1994 | Feldstein et al. |
| 5,447,728 A | 9/1995 | Milstein et al. |
| 5,451,410 A | 9/1995 | Milstein et al. |
| 5,541,155 A | 7/1996 | Leone-Bay et al. |
| 5,585,379 A | 12/1996 | Sintov et al. |
| 5,629,020 A | 5/1997 | Leone-Bay et al. |
| 5,643,957 A | 7/1997 | Leone-Bay et al. |
| 5,650,386 A | 7/1997 | Leone-Bay et al. |
| 5,665,700 A | 9/1997 | Cho et al. |
| 5,693,338 A | 12/1997 | Milstein |
| 5,705,529 A | 1/1998 | Matyus et al. |
| 5,709,861 A | 1/1998 | Santiago et al. |
| 5,714,167 A | 2/1998 | Milstein et al. |
| 5,747,537 A | 5/1998 | Gordon et al. |
| 5,750,147 A | 5/1998 | Kantor |
| 5,766,633 A | 6/1998 | Milstein et al. |
| 5,773,647 A | 6/1998 | Leone-Bay et al. |

(Continued)

FOREIGN PATENT DOCUMENTS

DE 3206030 9/1982

(Continued)

OTHER PUBLICATIONS

Schultz, Arnold G., et al., "Heteroatom Directed Photoarylation. Synthetic Potential of the Heteroatom Oxygen", Journal of the American Chemical Society 100(7): 2150-2162, Mar. 29, 1978.
Lakshminarayana et al, "Reaction of N-(4-Chlorobutyryl)isatin with Potassium Hydroxide", J.C.S. Perkin 1973; 1:998-1000.
Hakkarainen et al., "Liquid Crystaliine Behaviour of Some Carboxylic Acids", Polymer Bulltin, Springer Verlag 1993; 31(1):43-48.
Cassebaum, "Rontgenkonstrasrmittel Auf Der Basis Jodierter Phenoxyfettsauren", Pharmazie 1960; 15(6):310-316.
Gerecs et al., "Synthesen Aus Tetrahydrofurfurylalkohol, II", ACTA Chimica Acad. Sci Hung. 1958; 15(6):310-316.
Buckle et al., "Toxic Flourine Compounds Containing the C-F Link. Part VI. Omega-Fluorocarboxylic Acids and Derivatives", Journal of the Chemical Society 1949; 1471-1479.

(Continued)

Primary Examiner — Daniel M Sullivan
Assistant Examiner — Yevegeny Valenrod
(74) Attorney, Agent, or Firm — Blank Rome LLP

(57) ABSTRACT

Phenoxy carboxylic acid compounds and compositions for the delivery of active agents are provided. Methods of administration and preparation are provided as well.

15 Claims, No Drawings

U.S. PATENT DOCUMENTS

| | | | |
|---|---|---|---|
| 5,783,593 | A | 7/1998 | Baker et al. |
| 5,792,451 | A | 8/1998 | Sarubbi et al. |
| 5,811,127 | A | 9/1998 | Milstein et al. |
| 5,824,638 | A | 10/1998 | Burnside et al. |
| 5,837,702 | A | 11/1998 | Rovnyak et al. |
| 5,863,944 | A | 1/1999 | Leone-Bay et al. |
| 5,866,536 | A | 2/1999 | Leone-Bay et al. |
| 5,958,457 | A | 9/1999 | Santiago et al. |
| 5,990,166 | A | 11/1999 | Leone-Bay et al. |
| 6,001,347 | A | 12/1999 | Leone-Bay et al. |
| 6,051,258 | A | 4/2000 | Kantor |
| 6,051,561 | A | 4/2000 | Leone-Bay et al. |
| 6,060,513 | A | 5/2000 | Leone-Bay et al. |
| 6,071,510 | A | 6/2000 | Leone-Bay et al. |
| 6,071,538 | A | 6/2000 | Milstein et al. |
| 6,090,958 | A | 7/2000 | Leone-Bay et al. |
| 6,099,856 | A | 8/2000 | Milstein et al. |
| 6,100,285 | A | 8/2000 | Kantor |
| 6,100,298 | A | 8/2000 | Leone-Bay et al. |
| 6,180,140 | B1 | 1/2001 | Leone-Bay et al. |
| 6,221,367 | B1 | 4/2001 | Milstein et al. |
| 6,242,495 | B1 | 6/2001 | Leone-Bay et al. |
| 6,245,359 | B1 | 6/2001 | Milstein et al. |
| 6,313,088 | B1 | 11/2001 | Leone-Bay et al. |
| 6,331,318 | B1 | 12/2001 | Milstein |
| 6,344,213 | B1 | 2/2002 | Leone-Bay et al. |
| 6,346,242 | B1 | 2/2002 | Leone-Bay et al. |
| 6,348,207 | B1 | 2/2002 | Milstein et al. |
| 6,358,504 | B1 | 3/2002 | Leone-Bay et al. |
| 6,375,983 | B1 | 4/2002 | Kantor et al. |
| 6,395,774 | B1 | 5/2002 | Milstein |
| 6,399,798 | B2 | 6/2002 | Gschneidner et al. |
| 6,413,550 | B1 | 7/2002 | Milstein et al. |
| 6,444,213 | B1 | 9/2002 | Morita et al. |

FOREIGN PATENT DOCUMENTS

| | | |
|---|---|---|
| DE | 19915033 | 11/1999 |
| EP | 0036145 | 9/1981 |
| EP | 226223 | 6/1987 |
| EP | 0365183 | 4/1990 |
| EP | 0517211 | 12/1992 |
| EP | 548711 | 6/1993 |
| EP | 0555938 | 8/1993 |
| EP | 0576941 | 1/1994 |
| ES | 369853 A1 | 7/1971 |
| FR | 4446 A1 | 11/1966 |
| GB | 1502236 | 2/1978 |
| GB | 1529126 | 10/1978 |
| GB | 1586462 | 3/1981 |
| GB | 1586463 | 3/1981 |
| GB | 2095994 | 10/1982 |
| JP | 48-37819 | 11/1973 |
| JP | 2239980 | 9/1990 |
| RU | 1825378 | 6/1993 |
| SU | 170782 | 5/1965 |
| SU | 299048 | 8/1971 |
| SU | 544353 | 1/1977 |
| SU | 577256 | 10/1977 |
| SU | 656501 | 4/1979 |
| SU | 668569 | 6/1979 |
| SU | 730270 | 4/1980 |
| SU | 798091 | 1/1981 |
| SU | 824892 | 4/1981 |
| SU | 876058 | 10/1981 |
| WO | WO-88/07378 | 10/1988 |
| WO | WO-9747270 | 12/1997 |
| WO | WO-99/29705 A1 | 6/1999 |
| WO | WO-00/06481 | 2/2000 |
| WO | WO-0006184 | 2/2000 |
| WO | WO-0006534 | 2/2000 |
| WO | WO-0007979 | 2/2000 |
| WO | WO-0048589 | 8/2000 |
| WO | WO-0059863 | 10/2000 |

OTHER PUBLICATIONS

Sobotka et al., "p-Hydroxyphenoxy Aliphatic Acids", *Journal of the American Chemical Society* 1952; 74:3813-3815.

Riveria, Theresa M. et al., "Oral Delivery of Heparin in Combination with Sodium N-[8-2-hydroxybenzoyl)amino] caprylate: Pharmacological Considerations", *Pharmaceutical Research*, 1997; 14(12): 1830-1834.

Leone-Bay, Andrea, "4-(4-Salicyloylaminophenyl) butyric Acid as a Novel Oral Delivery Agent for Recombinant Human Growth Hormone", Medi 006, Presented at the American Chemical Society, Mar. 24-28, 1997 New Orleans, LA.

Leone-Bay, A. et al., "The evolution of an oral heparin dosing solution", *Drugs of the Future*, 1997; 22(8): 885-891.

Brayden, D. et al., "Heparin Absorption across the Intestine: Effects of Sodium N-[8-2hydroxybenzoyl)Amino] Caprylate in rat in situ intestimal istillations and in Caco-2 monolayers", Pharmaceutical Research, 19997; 14(12): 1772-1779.

Leone-Bay, A. et al., "Acylated non-alpha-amino acids as novel agents for the oral delivery of heparin sodium, USP", Journal of Controlled Release, 1998; 50: 41-49.

Leone-Bay, A. "4-[4-[(2-Hydroxybenzoyl)amino]phenyl]butyric acid as a novel oral delivery agent for recombinant human growth hormone", Journal of Medicinal Chemistry, 1996; 39: 2571-2578.

Leone-Bay, A., "N-Acylated alpha-amino acids as novel oral delivery agents for proteins", Journal of Medicinal Chemistry, 1995; 38: 4263-4269.

Koc-Kan et al., "A Practical Synthesis of □-aminoalkanoic acid derivatives from Cycloalkanones", Synthetic Communication, 1996; 26(14): 2641-2649.

Gurrieri and Siracusa, "Thermal Condensation of Some alpha-aminoacids with Phatalic Acid", Thermochimica Acta, 1973; 7: 231-239.

Yusuke et al., "Phenylalanine Derivatives Enhancing Intestinal Absorption of Insulin in Mice", Chem. Pharm. Bull., 1988; 36: 4426-4434.

Brown, G. and Foubister, A.J., "Receptor Binding Sites of Hypoglycemic Sulfonylureas and Related [(Acylamino)alkyl] benzoic Acids", J. Med. Chem., 27: 79-81.

Cassebarum, H., "Radiopaque media based on iodinated Phenoxy fatty acids", Cemical Abstracts 1964; 56: 7191.

Leone-Bay, A. et al., "Synthesis and Evaluation of Compounds that Facilitate the Gastrointestinal Absorption of Heparin", J. of Med. Chem., 1998; 41(7): 1163-1171.

Chem. Abstract RN 6324-11-4, Feb. 21, 2006.
Chem. Abstract RN 195394-50-4, Feb. 21, 2006.
Chem. Abstract RN 149288-38-0, Feb. 21, 2006.
Chem. Abstract RN 151042-01-2, Feb. 21, 2006.
Chem. Abstract RN 254116-46-6, Feb. 21, 2006.
Chem. Abstract RN 313486-59-8, Feb. 21, 2006.
Chem. Abstract RN 31719-76-3, Feb. 21, 2006.
Chem. Abstract RN 6303-58-8, Feb. 21, 2006.
Chem. Abstract RN 7170-40-3, Feb. 21, 2006.
Chem. Abstract RN 7305-69-3, Feb. 21, 2006.
Chem. Abstract RN 84822-51-5, Feb. 21, 2006.
Chem. Abstract RN 87706-88-5, Feb. 21, 2006.
Chem. Abstract RN 7305-68-2, Feb. 21, 2006.
Summary of Underlying References for Chem. Abstract RN 6324-11-4, Feb. 21, 2006.
Summary of Underlying References for Chem. Abstract RN 195394-50-4, Feb. 21, 2006.
Summary of Underlying References for Chem. Abstract RN 149288-38-0, Feb. 21, 2006.
Summary of Underlying References for Chem. Abstract RN 151042-01-2, Feb. 21, 2006.
Summary of Underlying References for Chem. Abstract RN 254116-46-6, Feb. 21, 2006.
Summary of Underlying References for Chem. Abstract RN 313486-59-8, Feb. 21, 2006.
Summary of Underlying References for Chem. Abstract RN 31719-76-3, Feb. 21, 2006.
Summary of Underlying References for Chem. Abstract RN 6303-58-8, Feb. 21, 2006.
Summary of Underlying References for Chem. Abstract RN 7170-40-3, Feb. 21, 2006.
Summary of Underlying References for Chem. Abstract RN 7305-69-3, Feb. 21, 2006.

Summary of Underlying References for Chem. Abstract RN 84822-51-5, Feb. 21, 2006.
Summary of Underlying References for Chem. Abstract RN 87706-88-5, Feb. 21, 2006.
Summary of Underlying References for Chem. Abstract RN 7305-68-2, Feb. 21, 2006.
International Search Report for International Application No. PCT/US00/30622 dated Apr. 4, 2001.
Picciola, "Sintesi Di Acidi Chiazolinioci E Benzonssazinonici E Studio Delle Loro Proprieta Antiniammatorie", IT Societa Chimica Italliana Pavia ; 31(9):655-664 and English Translation.
Chem. Abstract RN 73548-12-6, (Apr. 1991).
Chem. Abstract RN 70204-54-5, (Apr. 1991).
Chem. Abstract RN 184360-83-342, (1975), "Solubility and disassociation constants of some alicyclic acids".
Chemical Abstract, 99(23) Abst. No. 191473h (1983).
Chem. Abstract RN 6324-11-4.
Chem. Abstract RN 195394-50-4.
Chem. Abstract RN 122-59-8.
Chem. Abstract RN 6303-58-8.
Chem. Abstract RN 7170-38-9.
Chem. Abstract RN 7170-40-3.
Chem. Abstract RN 7170-41-4.
Chem. Abstract RN 7170-42-5.
Chem. Abstract RN 7305-69-3.
Chem. Abstract RN 7170-44-7.
Johansen et al., "The Kinetics of decompn. Of various N-Mannich bases of Salicylamide", Int. J. Pharm. 1980; 7(2):119-127.
Chem. Abstract 19847-26-8, (2002).
Wiley, "Amebacidal Chromanones," Journal of the American Chemical Society, vol. 73, 1951, p. 4205-4209.
Gerecs & Windholz, "Syntheses from Tetrahydrofurfuryl Alcohol," Acta Chimica Academiae Scientarum Hungaricae, vol. 16, 1958, p. 363-368.
Palagiano, F., et al., "Synthesis, Stability and Anticonvulsant Activity of Two New GABA Prodrugs," Pharamazic, 52 (4), 1997, p. 272-276, XP-001084051.
Yalcin, I. et al., "Synthesis, and Microbiological Activity of Some Novel N-(2-Hydroxyl-5-Substitutedphenyl) Benzacetamides, Phenoxyacetamides and Thiophenoxycetamides as the Possible Metabolites of Antimicrobial Active Benzoxazoles," IL Farmaco, 52 (11), 1997, p. 685-689.
Atwal, et al., J. Med. Chem., vol. 8, 1965, p. 566-571.
Harvey, et al., J. Chem. Soc. Perkin. Trans. 1, 1988, p. 681-689.
Ozaki, et al., Chem. Pharm. Bull., 31(7), 1983, p. 2234-2243.
Collins, et al., Tetrahedron, vol. 48, No. 37, 1992, p. 7887-7898.
Harvey, et al., J. Chem. Soc. Perkin Trans. I, 1988, p. 681-689.
Goudle, et al., J. Chem. Soc. □1971, p. 1139-1142.
Chemical Abstract vol. 79, 1973 (Columbus, OH) Abstract No. 18524, Lakshminarayana, P.J. Chem. Soc. Perkin Trans. 1 (1973), (10) 998-1000.

PHENOXY CARBOXYLIC ACID COMPOUNDS AND COMPOSITIONS FOR DELIVERING ACTIVE AGENTS

This application is a continuation of U.S. patent application Ser. No. 11/458,331, filed Jul. 18, 2006, now pending, which is a continuation of U.S. application Ser. No. 10/129,467, filed May 3, 2002, now U.S. Pat. No. 7,129,274, which is the national stage of International Application No. PCT/US00/30662, filed Nov. 6, 2000, which claims the benefit of U.S. Provisional Application No. 60/163,806 filed Nov. 5, 1999, U.S. Provisional Application No. 60/231,836 filed Sep. 6, 2000, and U.S. Provisional Application No. 60/237,233 filed Oct. 2, 2000, all of which are hereby incorporated by reference.

FIELD OF THE INVENTION

The present invention relates to phenoxy carboxylic acid compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula

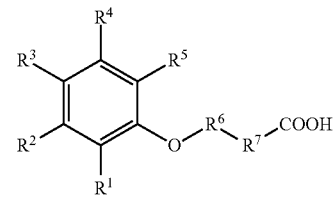

and salts thereof, wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}$ ($R^{12}$)$^-$;

$R^5$ is H, —OH, —$NO_2$, halogen, —$CF_3$, —$NR^{14}R^{15}$, —$N^+NR^{14}R^{15}R^{16}$ ($R^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;

$R^6$ is optionally interrupted by O or N;

$R^7$ is a bond or arylene;

$R^7$ is optionally substituted with —OH, halogen, —C(O)$CH_3$, —$NR^{10}R^{11}$, or —$N^+R^{10}R^{11}R^{12}$ ($R^{13}$)$^-$;

$R^8$ is H, $C_1$-$C_4$ alkyl, $C_2$-$C_4$ alkenyl, or —$NH_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —$NR^{14}R^{15}$, or $N^+R^{14}R^{15}R^{16}$ ($R^{13}$). with the proviso that when $R^1$, $R^2$, $R^3$, $R^4$, and $R^5$ are H, and $R^7$ is a bond then $R^6$ is not a $C_1$-$C_6$, $C_9$ or $C_{10}$ alkyl;

when $R^1$, $R^2$, $R^3$, and $R^4$ are H, $R^5$ is —OH, $R^7$ is a bond then $R^6$ is not a $C_1$-$C_3$ alkyl;

when at least one of $R^1$, $R^2$, $R^3$, and $R^4$ is not H, $R^5$ is —OH, $R^7$ is a bond, then $R^6$ is not a $C_1$-$C_4$ alkyl;

when $R^1$, $R^2$, and $R^3$ are H, $R^4$ is —OCH$_3$, $R^5$ is —C(O)CH$_3$, and $R^6$ is a bond then $R^7$ is not a $C_3$ alkyl; and when and $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ is a bond or para-phenylene. $R^7$ is more preferably a $C_7$-$C_9$ alkyl.

According to another preferred embodiment, at least one of $R^1$, $R^2$, $R^3$, and $R^4$ is hydrogen, —C(O)CH$_3$, —OH, Cl, —OCH$_3$, F, or —NO$_2$. In one more preferred embodiment, $R^2$ is —C(O)CH$_3$, —OH, —OCH$_3$, or —Cl. In another more preferred embodiment, $R^3$ is Cl, —OCH$_3$, F, or —OH. In yet another more preferred embodiment, $R^4$ is —OCH$_3$ or —NO$_2$.

According to yet another preferred embodiment, $R^5$ is —C(O)CH$_3$, —OH, H, —CH=CHCH$_3$, —NH$_2$, —NO$_2$, —NHC(O)CH$_3$, —CH=CHCO$_2$H, —C(O)CH$_2$CH$_3$, —C(O)NH$_2$, —C(O)NHCH$_3$, —COOH, —C(O)NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, $R^6$ is a linear $C_1$-$C_{12}$ alkylene. More preferably, $R^6$ is —(CH$_2$)$_n$—, where n is an integer from 1 to 10.

According to yet another preferred embodiment, $R^4$ and $R^5$ are not alkyl or halogen.

According to yet another preferred embodiment, $R^7$ is para-phenylene or a bond.

According to yet another preferred embodiment, $R^6$ is —CH$_2$— and $R^7$ is phenylene and, more preferably para-phenylene. More preferably, at least one of $R^1$, $R^2$, $R^3$, and $R^4$ is hydrogen. More preferably, $R^5$ is —C(O)CH$_3$, —OH or —C(CH$_3$)$_2$OH.

According to yet another preferred embodiment, $R^7$ is a bond, $R^5$ is —OH, and $R^1$, $R^2$, $R^3$, and $R^4$ are hydrogen. $R^6$ is preferably $C_4$-$C_{12}$ alkylene and, more preferably, $C_4$-$C_9$ alkylene.

According to yet another preferred embodiment, $R^7$ is a bond, $R^5$ is —OH, and at least one of $R^1$, $R^2$, $R^3$, and $R^4$ is not hydrogen. $R^6$ is preferably $C_1$-$C_{12}$ alkylene, more preferably $C_5$-$C_{12}$ alkylene, and most preferably $C_5$-$C_9$ alkylene.

According to yet another preferred embodiment, $R^7$ is a bond, $R^5$ is —C(O)CH$_3$, and $R^1$, $R^2$, $R^3$, and $R^4$ are hydrogen. $R^6$ is preferably $C_1$-$C_{12}$ alkylene, more preferably $C_3$-$C_{12}$ alkylene, and most preferably $C_3$-$C_7$ alkylene.

According to yet another preferred embodiment, $R^7$ is a bond and $R^1$, $R^2$, $R^3$, $R^4$ and $R^5$ are hydrogen. Preferably, $R^6$ is $C_7$-$C_9$ alkylene.

According to yet another preferred embodiment, $R^7$ is a bond, $R^5$ is hydrogen, and at least one $R^1$, $R^2$, $R^3$, and $R^4$ are not hydrogen. $R^6$ is preferably $C_1$-$C_{12}$ alkylene, more preferably $C_4$-$C_9$ alkylene, and most preferably $C_7$-$C_8$ alkylene.

According to yet another preferred embodiment, $R^2$ is —OH. More preferably, $R^7$ is a bond and $R^5$ is hydrogen. Preferably, $R^6$ is $C_1$-$C_{12}$ alkylene, more preferably $C_3$-$C_9$ alkylene, and most preferably $C_7$ alkylene.

According to yet another preferred embodiment, $R^3$ is —OH. More preferably, $R^7$ is a bond and $R^5$ is hydrogen. $R^6$ is preferably $C_1$-$C_{12}$ alkylene, more preferably $C_3$-$C_9$ alkylene, and most preferably $C_7$ alkylene.

Preferred delivery agent compounds include, but are not limited to, those described in Table 1 below, and salts thereof.

TABLE 1

| Cpd # | $R^1$ | $R^2$ | $R^3$ | $R^4$ | $R^5$ | $R^6$ | $R^7$ |
|---|---|---|---|---|---|---|---|
| 1 | H | H | H | H | C(O)CH$_3$ | CH$_2$ | para-Ph* |
| 2 | H | H | H | H | OH | CH$_2$ | para-Ph* |
| 3 | H | H | H | H | OH | CH$_2$ | bond |
| 4 | H | H | H | H | OH | (CH$_2$)$_3$ | bond |
| 5 | H | H | H | H | OH | (CH$_2$)$_5$ | bond |
| 6 | H | H | H | H | OH | (CH$_2$)$_6$ | bond |
| 7 | H | H | H | H | OH | (CH$_2$)$_7$ | bond |
| 8 | H | H | H | H | OH | (CH$_2$)$_9$ | bond |
| 9 | H | H | H | H | C(O)CH$_3$ | (CH$_2$)$_3$ | bond |
| 10 | H | H | H | H | C(O)CH$_3$ | (CH$_2$)$_4$ | bond |
| 11 | H | H | H | H | C(O)CH$_3$ | (CH$_2$)$_5$ | bond |
| 12 | H | H | H | H | C(O)CH$_3$ | (CH$_2$)$_7$ | bond |
| 13 | H | H | H | H | H | CH$_2$ | bond |
| 14 | H | H | H | H | H | (CH$_2$)$_3$ | bond |
| 15 | H | H | H | H | H | (CH$_2$)$_5$ | bond |
| 16 | H | H | H | H | H | (CH$_2$)$_9$ | bond |
| 17 | H | H | H | H | H | (CH$_2$)$_{10}$ | bond |
| 18 | H | H | H | H | CH=CHCH$_3$ | (CH$_2$)$_7$ | bond |
| 19 | H | H | H | H | NH$_2$ | (CH$_2$)$_7$ | bond |
| 20 | H | H | H | H | NO$_2$ | (CH$_2$)$_7$ | bond |
| 21 | H | H | H | H | NH$_2$ | (CH$_2$)$_4$ | bond |
| 22 | H | H | Cl | H | NH$_2$ | (CH$_2$)$_4$ | bond |
| 23 | H | H | Cl | H | NH$_2$ | (CH$_2$)$_4$ | bond |
| 24 | H | H | H | H | NHC(O)CH$_3$ | (CH$_2$)$_7$ | bond |
| 25 | H | H | H | H | CH=CHCO$_2$H | (CH$_2$)$_7$ | bond |
| 26 | H | H | H | H | C(O)CH$_2$CH$_3$ | (CH$_2$)$_3$ | bond |
| 27 | H | H | H | H | C(O)CH$_2$CH$_3$ | (CH$_2$)$_5$ | bond |
| 28 | H | H | H | H | C(O)CH$_2$CH$_3$ | (CH$_2$)$_7$ | bond |
| 29 | H | H | H | H | C(O)CH$_2$CH$_3$ | (CH$_2$)$_9$ | bond |
| 30 | H | H | H | H | C(O)NH$_2$ | (CH$_2$)$_7$ | bond |
| 31 | H | H | H | H | C(O)NHCH$_3$ | (CH$_2$)$_7$ | bond |
| 32 | H | H | H | H | COOH | (CH$_2$)$_7$ | bond |
| 33 | H | H | H | H | C(O)NHCH$_2$CH$_3$ | (CH$_2$)$_7$ | bond |
| 34 | H | H | H | H | C(O)NHCH(CH$_3$)$_2$ | (CH$_2$)$_7$ | bond |
| 35 | H | H | H | H | OCH$_3$ | (CH$_2$)$_7$ | bond |

TABLE 1-continued

| Cpd # | $R^1$ | $R^2$ | $R^3$ | $R^4$ | $R^5$ | $R^6$ | $R^7$ |
|---|---|---|---|---|---|---|---|
| 36 | H | H | H | H | CH(OH)CH$_3$ | (CH$_2$)$_7$ | bond |
| 37 | H | H | H | H | C(CH$_3$)$_2$OH | CH$_2$ | para-Ph* |
| 38 | H | H | H | OH | C(O)CH$_3$ | (CH$_2$)$_7$ | bond |
| 39 | H | H | H | OCH$_3$ | C(O)CH$_3$ | (CH$_2$)$_7$ | bond |
| 43 | H | OH | H | H | H | (CH$_2$)$_7$ | bond |
| 44 | H | OH | H | H | H | (CH$_2$)$_9$ | bond |
| 45 | H | OH | H | H | H | (CH$_2$)$_5$ | bond |
| 46 | H | OH | H | H | H | (CH$_2$)$_3$ | bond |
| 47 | H | H | OH | H | H | (CH$_2$)$_7$ | bond |
| 48 | H | H | OH | H | H | (CH$_2$)$_9$ | bond |
| 49 | H | H | OH | H | H | (CH$_2$)$_5$ | bond |
| 50 | H | H | OH | H | H | (CH$_2$)$_3$ | bond |
| 51 | H | H | H | H | C(O)NHCH$_3$ | (CH$_2$)$_9$ | bond |
| 52 | H | H | H | H | C(O)NH$_2$ | CH$_2$ | para-Ph* |
| 54 | H | H | H | H | C(O)CH$_3$ | (CH$_2$)$_9$ | bond |
| 55 | H | H | OCH$_3$ | H | C(O)CH$_3$ | (CH$_2$)$_7$ | bond |
| 56 | H | OCH$_3$ | H | H | C(O)CH$_3$ | (CH$_2$)$_7$ | bond |
| 57 | H | H | OH | H | C(O)CH$_3$ | (CH$_2$)$_7$ | bond |
| 58 | H | H | CH$_3$ | H | C(O)CH$_3$ | (CH$_2$)$_5$ | bond |
| 59 | H | H | H | H | C(O)H | CH$_2$ | para-Ph* |
| 60 | H | H | H | H | C(O)H | (CH$_2$)$_5$ | bond |
| 61 | H | H | H | H | C(O)H | (CH$_2$)$_7$ | bond |
| 62 | H | H | C(O)CH$_3$ | H | H | (CH$_2$)$_7$ | bond |
| 63 | H | H | C(O)CH$_2$CH$_3$ | H | H | (CH$_2$)$_7$ | bond |
| 64 | H | C(O)CH$_3$ | H | H | H | (CH$_2$)$_7$ | bond |
| 65 | H | H | H | H | H | (CH$_2$)$_7$ | bond |
| 66 | H | H | H | H | H | CH$_2$ | para-Ph* |
| 67 | H | H | OH | H | H | CH$_2$ | para-Ph* |
| 68 | H | Cl | H | H | H | (CH$_2$)$_7$ | bond |
| 69 | H | H | OCH$_3$ | H | H | (CH$_2$)$_7$ | bond |
| 71 | H | H | F | H | F | (CH$_2$)$_7$ | bond |
| 72 | H | H | H | H | OH | (CH$_2$)$_{10}$ | bond |
| 73 | H | H | H | H | Cl | (CH$_2$)$_7$ | bond |
| 74 | H | NO$_2$ | H | H | OH | (CH$_2$)$_7$ | bond |
| 75 | H | H | H | H | F | (CH$_2$)$_4$ | bond |
| 76 | H | H | H | H | CF$_3$ | (CH$_2$)$_4$ | bond |
| 77 | F | H | H | H | F | (CH$_2$)$_7$ | bond |
| 78 | H | H | H | H | Cl | CH$_2$ | para-Ph* |
| 79 | H | H | H | H | OH | CH$_2$CH(OH) | para-Ph* |
| 80 | H | H | OCH$_3$ | H | H | (CH$_2$)$_6$—CH(CH$_3$) | bond |
| 81 | H | H | OH | H | H | (CH$_2$)$_6$—CH(CH$_3$) | bond |
| 82 | H | H | OH | H | H | (CH$_2$)$_6$—CH(CH$_2$CH$_2$CH$_3$) | bond |
| 88 | H | H | H | H | —C(O)NH—(CH$_2$)$_9$—OH | CH$_2$ | bond |
| 92 | H | H | H | H | —O(CH$_2$)$_5$COOH | (CH$_2$)$_5$ | bond |
| 93 | H | CH$_3$ | H | H | CH$_3$ | (CH$_2$)$_7$ | bond |
| 94 | H | CH$_3$ | H | H | CH$_3$ | (CH$_2$)$_5$ | bond |
| 95 | H | H | NO$_2$ | H | H | para-Ph | bond |
| 96 | H | H | NH$_2$ | H | H | para-Ph | bond |
| 97 | H | CH$_3$ | H | H | CH$_3$ | (CH$_2$)$_3$—(C(CH$_3$)$_2$) | bond |
| 98 | H | H | H | C(O)—NH$_2$ | O—(CH$_2$)$_7$—COOH | —(CH$_2$)$_7$— | bond |

*The term "para-Ph" represents para-phenylene.

More preferred compounds include, but are not limited to, compound nos. 5, 7, 11, 12, 43, and 47.

The invention also provides a composition comprising at one of the delivery agent compounds of the formula above, including those compounds excluded by proviso, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds of the formula above, including those compounds excluded by proviso, and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formula above, including those compounds excluded by proviso, and at least one active agent.

DETAILED DESCRIPTION OF THE INVENTION

Delivery Agent Compounds

The terms "alkyl" and "alkenyl" as used herein include linear and branched alkyl and alkenyl substituents, respectively.

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium;

ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. A preferred disodium salt is the disodium salt of compound 47. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of mucopolysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

A preferred active agent is daptomycin. Daptomycin is described by Baltz in *Biotechnology of Antibiotics, 2$^{nd}$ Ed.*, ed. W. R. Strohl (New York: Marcel Dekker, Inc.), 1997, pp. 415-435. Daptomycin is a cyclic lipopeptide antibiotic that can be derived from the fermentation of *Streptomyces roseosporus*. Daptomycin is a member of the factor A-21978$C_0$ type antibiotics of *S. roseosporus* and comprises a n-decanoyl side chain linked via a three-amino acid chain to the N-terminal tryptophan of a cyclic 10-amino acid peptide. The compound is currently being developed in a variety of formulations to treat serious infections caused by bacteria, including, but not limited to, methicillin resistant *Staphylococcus aureus* (MRSA) and vancomycin resistant enterococci (VRE). Methods for synthesizing daptomycin are described in U.S. Pat. Nos. Re. 32,333; Re. 32,455; 5,800, 157, 4,885,243; Re. 32,310; Re. 32,311; 4,537,717; 4,482, 487 and 4,524,135.

Delivery Systems

The composition of the present invention comprises one or more delivery agent compounds of the present invention, including those excluded by proviso, and one or more active agents. The delivery agent compound and active agent are typically mixed prior to administration to form an administration composition.

Preferred combinations of delivery agent compounds and active agents include, but are not limited to, compound 12 and calcitonin, and in particular salmon calcitonin; compound 12 and heparin; compound 5 and calcitonin, and in particular salmon calcitonin; any one of compounds 7, 11, and 43 and daptomycin; compound 7 and cromolyn, and in particular cromolyn sodium; and compound 47 and human growth hormone.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
|---|---|
| Growth hormones, including human growth hormones (hGH), recombinant human growth hormones (rhGH), bovine growth hormones, and porcine growth hormones; growth hormone-releasing hormones. | Growth disorders |
| Interferons, including α, β and γ. | Viral infection, including chronic cancer and multiple sclerosis |
| Interleukin-1; interleukin-2. | Viral infection; cancer |
| Insulin, including porcine, bovine, human, and human recombinant, optionally having counter ions including zinc, sodium, calcium and ammonium; insulin-like growth factor, including IGF-1. | Diabetes |
| Heparin, including unfractionated heparin, heparinoids, dermatans, chondroitins, low molecular weight heparin, very low molecular weight heparin and ultra low molecular weight heparin. | Thrombosis; prevention of blood coagulation |
| Calcitonin, including salmon, eel, porcine and human. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium (sodium or disodium chromoglycate); vancomycin | Asthma; allergies |
| Desferrioxamine (DFO) | Iron overload |
| Parathyroid hormone (PTH), including its fragments. | Osteoporosis; diseases of the bone |
| Antimicrobials, including antibiotics, anti-bacterials and anti-fungal agents; gram-positive acting, | Infection including gram-positive bacterial infection |

-continued

| Active Agent | Disease and Physiological Effect |
|---|---|
| bacteriocidal, lipopeptidal and cyclic peptidal antibiotics, and includes daptomycin and analogues thereof | |
| Vitamins | Vitamin deficiencies |
| Bisphosphonates, including alendronate, tiludronate, etidronate, clodronate, pamidronate, olpadronate, and incadronate | Osteoporosis and Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

Example 1

Compound Preparation

Preparation of Compound 1

Potassium hydroxide (8.82 g, 157.2 mmol) was ground in a mortar until powdered, then added to a 125 mL Erlenmeyer flask containing 60 mL of dimethyl sulfoxide. The resulting mixture was stirred for 5 minutes, after which time 5.35 g (39.3 mmol) of 2'-hydroxyacetophenone was added. The mixture was stirred an additional 15 minutes, after which time 5.39 g (25.1 mmol) of 4-(bromomethyl)benzoic acid was added. The reaction was stirred at room temperature for about four hours. Distilled water (200 mL) was added to the brown reaction mixture, and the resulting solution was cooled to 0° C. Concentrated aqueous hydrochloric acid was added until the pH of the solution was about 5. The resulting solid was collected by filtration and recrystallized from 50:50 (ethanol: water) to give 3.59 g (52.9%) of a light brown powder. Melting point: 170.5-172.0° C. Combustion analysis: % C, 71.10 (calc'd), 70.81 (found); % H, 5.22 (calc'd), 5.25 (found). $^1$H NMR Analysis: ($d_6$-DMSO): δ 13.0, s, 1H, 8.00-7.97, d, 2H, 7.64-7.59, m, 3H, 7.55-7.49, dt, 1H, 7.25-7.22, d, 1H, 7.07-7.01, dt, 1H, 5.33, s, 2H, 2.54, s, 3H.

Compounds 63, 62, and 64 were prepared by this method using the appropriate starting materials with the appropriate starting materials.

Compound 63. Melting point: 91-94° C. Combustion analysis: % C, 69.62 (calc'd), 69.91 (found); % H, 8.53 (calc'd), 8.28 (found); $^1$H NMR Analysis: ($d_6$-DMSO): δ 12.0, bs, 1H, 7.9, d, 2H, 7.0, d, 2H, 4.0, t, 2H, 3.0, q, 2H, 2.2, t, 2H, δ 1.7, p, 2H, 1.5, p, 2H, 1.35, m, 6H, 1.05, t, 3H.

Compound 62: Melting point: 125-129° C. Combustion analysis: % C, 69.04 (calc'd), 68.91 (found); % H, 7.97 (calc'd), 8.04 (found); $^1$H NMR Analysis: ($d_6$-DMSO): δ 12.0, bs, 1H, 7.9, d, 2H, 7.02, d, 2H, 4.01, t, 2H, 2.52, s, 3H, 2.23, t, 2H, 1.7, p, 2H, 1.5, p, 2H, 1.38, m, 6H.

Compound 64. Melting point: 62-65° C. Combustion analysis: % C, 69.06 (calc'd), 69.32 (found); % H: 7.91 (calc'd), 7.97 (found); $^1$H NMR Analysis: ($d_6$-DMSO) δ 12.0, s, 1H, 7.5, d, 1H, 7.4, m, 2H, 7.19, dd, 1H, 4.02, t, 2H, 2.55, s, 3H, 2.2, t, 2H, 1.7, p, 2H, 1.5, p, 2H, 1.3, m, 6H.

Compounds 66 and 52 were also made by the method used to prepare Compound 1, replacing 2'-hydroxy-acetophenone with the compound listed in parentheses: 66 (phenol), and 52 (salicylamide).

Compound 66: Melting point: 219-221° C. Combustion analysis: % C, 73.67 (calc'd), 73.70 (found); % H 5.30 (calc'd), 5.22 (found). $^1$H NMR Analysis: ($d_6$-DMSO): δ 13.0, s, 1H, 7.97, d, 2H, 7.57, d, 2H, 7.30, m, 2H, 7.01, m, 2H, 6.95, m, 1H, 5.19, s, 2H.

Compound 52: Melting point: 242-243° C. Combustion analysis: % C, 66.08 (calc'd), 65.74 (found); % H 4.86 (calc'd), 4.79 (found); % N 5.14 (calc'd), 4.78 (found). $^1$H NMR Analysis: ($d_6$-DMSO): δ 13.0, s, 1H, 7.97, d, 2H, 7.75, dd, 1H, 7.64, bs, 1H, 7.62, d, 2H, 7.56, bs, 1H, 7.44, dt, 1H, 7.17, d, 1H, 7.03, t, 1H, 5.35, s, 2H.

Preparation of Compound 2

Potassium hydroxide (9.88 g, 176 mmol) was ground in a mortar until powdered, then added to a 125 mL Erlenmeyer flask containing 80 mL of dimethyl sulfoxide and 5.54 g (50.3 mmol) of catechol. The resulting mixture was stirred for 45 minutes, heating slightly to 35° C. The dark mixture was treated with a solution of 6.94 g (40.7 mmol) of 4-(chloromethyl)benzoic acid and 30 ml of dimethyl sulfoxide. The reaction was stirred at room temperature for about 17 hours. Acidification with 4% aqueous hydrochloric acid caused a solid to develop. The solid was collected by filtration. Recrystallization from ethyl acetate/methyl t-butyl ether/hexanes and flash chromatography using 70% hexanes/ethyl acetate/ 1% acetic acid, as eluant, gave compound 2 as a white solid (1.10 g (11% yield)). Melting point: 196-198° C. Combustion analysis: % C, 68.85 (calc'd), 68.60 (found); % H, 4.95 (calc'd), 4.82 (found). $^1$H NMR Analysis: ($d_6$-DMSO): δ 12.96, s, 1H, 9.03, s, 1H, 7.97 d, 2H, 7.61, d, 2H, 6.95, dd, 1H, 6.83, dd, 1H, 6.78, td, 1H, 6.70, dt, 1H, 5.18, s, 2H.

Compound 79 and 59 were prepared in the same manner as in Compound 2.

Compound 79: Melting point: 176-8° C. Combustion analysis: % C, 65.69 (calc'd), 65.53 (found); % H, 5.15 (calc'd), 5.00 (found); $^1$H NMR Analysis: ($d_6$-DMSO): δ 13.0, bs, 1H, 8.7, bs, 1H, 7.9, d, 2H, 7.6, d, 2H, 6.9, d, 1H, 6.75, m, 2H, 6.7, m, 1H, 5.9, bs, 1H, 5.0, m, 1H, 4.1, dd, 1H, 3.85, dd, 1H.

Compound 59: Melting point: 164-7° C. Combustion analysis: % C, 70.31 (calc'd), 70.18 (found); % H, 4.72 (calc'd), 4.83 (found); $^1$H NMR Analysis: ($d_6$-DMSO): δ 13.0, bs, 1H, 10.5, s, 1H, 8.7, bs, 1H, 7.9, d, 2H, 7.6, d, 2H, 6.9, d, 1H, 6.75, m, 2H, 6.7, m, 1H, 5.9, bs, 1H, 5.0, m, 1H, 4.1, dd, 1H, 3.85, dd, 1H.

Preparation of Compound 3

Compound 3 was purchased from Lancaster Synthesis Inc. (Windham, N.H.)

Preparation of Compound 6

A 200 mL round bottom flask was charged with 11.2 g (4 equiv) of powdered potassium hydroxide and 100 mL of dimethyl sulfoxide. This mixture was stirred at room temperature for 5 minutes. 2-Benzyloxyphenol (10 g, 1 equiv.) was added followed immediately by addition of ethyl 7-bromoheptanoate (14.6 mL, 1.5 equiv). The resulting solution was stirred at room temperature for 1 hour.

The reaction mixture was poured into 200 mL of distilled water and extracted with 5×100 mL of methylene chloride. The combined organic layers were then washed with water and brine (20 mL each) and concentrated. This liquid was then dissolved in 125 mL of aqueous methanol. Solid sodium hydroxide (3 equiv., 3.7 g) was added and the resulting solution was heated to 80° C. for 2 hours. The mixture was cooled to room temperature and the methanol evaporated. The aqueous layer was extracted with 150 mL ether, then acidified to pH ~2 with concentrated aqueous hydrochloric acid. The aqueous layer was extracted with ethyl acetate (2×300 mL), filtered and dried to give 19 g of (2-benzyloxyphenyl) 7-oxyheptanoic acid.

A slurry of (2-benzyloxyphenyl)-7-oxy-heptanoic acid (19 g, 58 mmol), 150 mL of ethyl alcohol, and 150 mg of palladium black was prepared and placed in a Parr autoclave. The reaction vessel was pressurized to 100 psi with hydrogen. The mixture was stirred at 50° C. for 17 hours. The palladium was filtered and the filtrate concentrated to give the product as a pale yellow solid. The crude material was purified by silica gel chromatography using 30-60% ethyl acetate/hexanes as eluent to give 5 g (42%) of (2-hydroxyphenyl)-7-oxyheptanoic acid as an off-white solid. Melting point: 47-50° C. Combustion analysis: % C, 65.53 (calc), 65.12 (found); % H, 7.61 (calc), 7.82 (found). EI-MS: 238 (calc), 238 (found). $^1$H NMR Analysis: ($d_6$-DMSO): δ 12.0, 8, 1H, 8.8, s, 1H, 6.89-6.86, m, 1H, 6.80-6.87, m, 3H, 3.94, t, 2H, 2.21, t, 2H, 1.72-1.67, m, 2H, 1.55-1.25 m, 6H.

Preparation of Compound 7

A 200 mL round bottom flask was charged with 22.9 g (3 equiv.) of freshly ground potassium hydroxide and 100 mL of dimethyl sulfoxide. This mixture was stirred at 25° C. for 5 minutes. Catechol (15 g, 1 equiv.) was added followed immediately by ethyl 8-bromooctanoate (34.2 g, 1 equiv). This dark brown solution was then stirred at 25° C. for 2 hours.

Distilled water (100 mL) was added and this solution was heated to 85° C. for 2 hours. The mixture was cooled, acidified to pH ~2 with concentrated aqueous hydrochloric acid, and extracted with ethyl acetate (300 mL×2). The combined organics were dried over magnesium sulfate, filtered and the solvent evaporated. The crude material was purified by silica gel chromatography using 30-60% ethyl acetate/hexanes as eluent. The desired product was collected and dried to give 6.6 g (19%) of 8-(2-hydroxyphenoxy)octanoic acid as an off-white solid. Melting point: 60-64° C. Combustion analysis: % C, 66.65 (calc'd), 66.65 (found); % H, 7.99 (calc'd), 8.10 (found). $^1$H NMR Analysis: ($d_6$-DMSO): δ 12.0 s, 1H, 8.8, s, 1H, 6.90-6.86, m, 1H, 6.80-6.76, m, 3H, 3.92, t, 2H, 2.21 t, 2H, 1.75-1.66, m, 2H, 1.56-1.29, m, 8H.

Compounds 4, 35, 38, 92, and 98 were also prepared by this method using the appropriate starting materials.

Compound 4: Melting point: 64-66° C. Combustion analysis: % C, 61.22 (calc'd), 61.32 (found); % H 6.16 (calc'd), 6.27 (found). $^1$H NMR Analysis: ($d_6$-DMSO): δ 12.1, s, 1H, 8.75, s, 1H, 6.90-6.87, m, 1H, 6.81-6.68, m, 3H, 3.98, t, 2H, 2.51, t, 2H, 1.98-1.89, m, 2H.

Compound 35: Melting point: 77-80° C. Combustion analysis: % C, 67.65 (calc'd), 67.40 (found); % H, 8.33 (calc'd), 8.37 (found). $^1$H NMR Analysis: ($d_6$-DMSO): δ 11.9, s, 1H, 6.96-6.85, m, 4H, 3.94, t, 2H, 3.74, s, 3H, 2.23, t, 2H, 1.72-1.65, m, 2H, 1.53-1.48, m, 2H, 1.39-1.29, m, 6H.

Compound 38: Melting point: 75-76° C. Combustion analysis: % C, 65.29 (calc'd), 65.42 (found); % H, 7.53 (calc'd), 7.47 (found). $^1$H NMR Analysis: ($d_6$-DMSO): δ 12.0, s, 1H, 11.9, s, 1H, 7.35, t, 1H, 6.56, dd, 2H, 4.04, t, 2H, 2.55, s, 3H, 2.27, t, 2H, 1.79-1.70, m, 2H, 1.55-1.48, m, 2H, 1.45-1.37, m, 2H, 1.32-1.14, m, 4H.

Compound 92: Melting point: 107-8° C. Combustion analysis: % C, 63.89 (calc'd), 63.98 (found); % H, 7.74 (calc'd), 7.72 (found); $^1$H NMR Analysis: ($d_6$-DMSO): δ 12.0, bs, 2H, 6.95, m, 2H, 6.85, m, 2H, 3.9, t, 4H, 3.0, q, 2H, 2.2, t, 4H, δ 1.7, p, 4H, 1.55, p, 4H, δ 1.4, p, 4H.

Compound 98: Melting point: 75-77° C. Combustion analysis: % C, 63.16 (calc'd), 62.81 (found); % H, 8.01 (calc'd), 8.17 (found); % N, 3.2 (calc'd), 3.05 (found). $^1$H NMR Analysis: ($d_6$-DMSO): δ 12.0, s, 2H, 7.60, s, 1H, 7.45, s, 1H, 7.03-7.21, m, 3H, 3.9, m, 4H, 2.14, t, 4H, 1.61, m, 4H, 1.22-1.55, m, 16H.

Alternate Preparation of Compound 7

A 500 mL Erlenmeyer flask was charged with 28 g (4 equiv.) of powdered potassium hydroxide and 400 mL of dimethyl sulfoxide. This mixture was stirred at room temperature for 5 minutes. 2-Benzyloxyphenol (25 g, 1 equiv.) was added and followed immediately by addition of ethyl 8-bromooctanoate (37.6 g, 1.2 equiv). The resulting solution was stirred at room temperature for 2 hours.

The reaction mixture was poured into 200 mL of distilled water and heated to 80° C. for 3 hours. This mixture was then acidified with concentrated aqueous hydrochloric acid to a pH of approximately 2. An off-white solid precipitated. This solid was isolated by vacuum filtration and allowed to dry overnight at room temperature in vacuo. The material was then esterified by reacting the crude acid with 1 L of methanol and 5 mL of sulfuric acid and subsequent heating to 80° C. overnight. The mixture was cooled and extracted with ethyl acetate 3×400 mLs, dried over magnesium sulfate, filtered and evaporated to give the methyl ester in quantitative yield.

The crude ester was then dissolved in 150 mL of ethanol and mixed with 1 g of 10% palladium on activated carbon. This mixture was placed in the Parr autoclave. The reaction vessel was then pressurized to 200 psi with hydrogen. The heterogeneous mixture was stirred at 50° C. for 18 hours. The palladium was filtered off and the filtrate concentrated to give the debenzylated product.

The methyl ester was saponified using 10 g of sodium hydroxide, 400 mL of methanol, and 50 mL of water. The solution was heated to 80° C. for one hour, and then allowed to stir at ambient temperature overnight. The methanol was evaporated. An additional 100 mL of water was added and the aqueous layer acidified with concentrated aqueous hydrochloric acid to a pH of 2. The aqueous phase was then extracted with ethyl acetate, 3×300 mL, dried and evaporated to give the target material. The crude material was then purified by silica gel chromatography using 30-60% ethyl acetate/ hexanes, as eluent, to give 22.24 g (71%) of 8-(2-hydroxyphenoxy)octanoic acid as an off-white solid. Melting point:

65-68° C. Combustion analysis: % C, 66.65 (calc'd), 66.98 (found); % H, 7.99 (calc'd) 8.22 (found).

$^1$H NMR Analysis: (d$_6$-DMSO): δ 12.0, s, 1H, 8.8, s, 1H, 6.90-6.87, m, 1H, 6.80-6.67, m, 3H, 3.94, t, 2H, 2.23, t, 2H, 1.73, p, 2H, 1.53-1.29, m, 8H.

Compounds 5, 8, and 72 were also prepared by this method using the appropriate starting materials.

Compound 5: Melting point: 51-53° C. Combustion analysis: % C, 64.27 (calc'd), 64.26 (found); % H 7.19 (calc'd), 7.00 (found). $^1$H NMR Analysis: (d$_6$-DMSO): δ 12.0, bs, 1H, 8.80, bs, 1H, 6.90-6.85, m, 1H, 6.80-6.68, m, 3H, 3.94, t, 2H, 2.26, t, 2H, 1.76-1.67, m, 2H, 1.61-1.52, m, 2H, 1.48-1.40, m, 2H.

Compound 8: Melting point: 54-57° C. Combustion analysis: % C, 68.55 (calc'd), 68.78 (found); % H 8.63 (calc'd), 8.43 (found). $^1$H NMR Analysis: (d$_6$-DMSO): δ 8.8, bs, 1H, 6.92-6.89, m, 1H, 6.82-6.71, m, 3H, 3.96, t, 2H, 2.24, t, 2H, 1.75-1.68, m, 2H, 1.54-1.39, m, 4H, 1.30, bs, 8H.

Compound 72. Melting point: 58-60° C. Combustion analysis: % C, 69.36 (calc'd), 69.12 (found); % H, 8.90 (calc'd), 8.89 (found). $^1$H NMR Analysis: (d$_6$-DMSO): δ 6.88-6.85, m, 1H, 6.80-6.66, m, 3H, 3.93, t, 2H, 2.20, t, 2H, 1.74-1.65, m, 2H, 1.50-1.35, m, 4H, 1.25, bs, 10H.

Preparation of Compound 12

Potassium hydroxide (10.72 g, 191.1 mmol) was ground in a mortar until powdered, then added to a 250 mL round bottom flask containing 80 mL of dimethyl sulfoxide. The resulting mixture was stirred for 5 minutes, after which time 6.47 g (47.5 mmol) of 2-hydroxyacetophenone was added, immediately followed by 24.04 g (95.7 mmol) of ethyl 8-bromooctanoate. The reaction was stirred at room temperature for one hour. The orange reaction mixture was poured into 200 mL of distilled water, then extracted five times with 300 mL (total) of methylene chloride. The organic layers were washed with two 50 mL portions of water, then concentrated to give a bright yellow liquid.

The liquid was dissolved in 25 mL of dioxane. Aqueous sodium hydroxide (1N, 20 mL) was added, and the resulting liquid was stirred and heated (65° C.) for two hours. The reaction mixture was cooled to 0° C., acidified to pH 1 with concentrated aqueous hydrochloric acid, then extracted with two 100 mL portions of ethyl acetate. The organic layer was concentrated to give a bright yellow oil. The oil was crystallized with methanol:water (1:1), then recrystallized once with methanol:water (1:1), and once with methylene chloride:hexanes (1:4), to give 5.70 g (43.1%) of a pale yellow to off white solid. Melting point: 71.5-73.5° C. Combustion analysis: % C, 69.04 (calc'd), 68.77 (found); % H, 7.97 (calc'd), 8.04 (found). $^1$H NMR Analysis: (d$_6$-DMSO): δ 12.0, s, 1H, 7.57, dd, 1H, 7.52, dt, 1H, 7.15, d, 1H, 7.00, dt, 1H, 4.09, t, 2H, 2.52, s, 3H, 2.20, t, 2H, 1.78, p, 2H, 1.46, m, 4H, 1.32, m, 4H.

Compounds 9, 10, 11 and 71 were also prepared by this method using the appropriate starting materials.

Compound 9: Melting point: 94.5-9° C. Combustion analysis: % C, 64.85 (calc'd), 64.81 (found); % H, 6.35 (calc'd), 6.30 (found). $^1$H NMR (300 MHz, d$_6$-DMSO): δ 12.0 (s, 1H), 7.58, dd, 1H, 7.5, dt, 1H, 7.15, dd, 1H, 7.0, dt, 1H, 4.15, t, 2H, 2.55, s, 3H, 2.45, t, 2H, 2.0, p, 2H.

Compound 10: Melting point: 76-7° C.; Combustion analysis: % C, 66.09 (calc'd), 65.83 (found); % H, 6.83 (calc'd), 6.76 (found). $^1$H NMR (300 MHz, DMSO-d$_6$): δ 7.58, dd, 1H, 7.5, dt, 1H, 7.15, dd, 1H, 7.0, dt, 1H, 4.1, t, 2H, 2.55, s, 3H, 2.3, t, 2H, 1.8, dp, 2H, 1.6, dp, 2H.

Compound 11: Melting point: 44-4° C. Combustion analysis: % C, 67.18 (calc'd), 67.32 (found); % H 7.25 (calc'd), 7.26 (found). $^1$H NMR (300 MHz, d$_6$-DMSO): δ 12.0, s, 1H, 7.58, dd, 1H, 7.5, dt, 1H, 7.15, d, 1H, 7.0, t, 1H, 4.1, t, 2H, 2.55, s, 3H, 2.25, t, 2H, 1.8, p, 2H, 1.6, p, 2H, 1.45, p, 2H.

Compound 71. Melting point: 61-63° C. Combustion analysis: % C, 61.76 (calc'd), 61.69 (found); % H, 6.66 (calc'd), 6.59 (found). $^2$H NMR Analysis: (d$_6$-DMSO): δ 12.0, br. s, 1H, 7.13-7.30, m, 2H, 6.94-7.02, m, 1H, 3.98-4.02, t, 2H, 2.17-2.22, t, 2H, 1.65-1.72, m, 2H, 1.28-1.52, m, 8H.

The following compounds were also prepared by this method, replacing 2'-hydroxyacetophenone with the compound listed in parentheses: 18 (2-propenylphenol), 20 (2-nitrophenol), 24 (2-acetamidophenol), 26-29 (2-hydroxypropiophenone), 32 (methyl salicylate) and 39 (6-methoxy-2-hydroxy-acetophenone). Compounds 18 and 20 were further purified by column chromatography using 50% ethyl acetate in hexanes as the eluent.

Compound 18: Melting point: 79-81° C. Combustion analysis: % C, 73.88 (calc'd), 73.85 (found); % H, 8.75 (calc'd), 8.77 (found). $^1$H NMR Analysis: (d$_6$-DMSO): δ 12.0, s, 1H, 7.38-7.41, dd, 1H, 7.13-7.18, m, 1H, 6.93-6.95, d, 1H, 6.84-6.89, t, 1H, 6.59-6.65, dd, 1H, 6.21-6.28, m, 1H, 3.94-3.98, t, 2H, 2.18-2.23, t, 2H, 1.83-1.86, dd, 2H, 1.69-1.78, m, 2H, 1.31-1.53, m, 9H.

Compound 20: Melting point: 81-8° C. Combustion analysis: % C, 59.78 (calc'd), 59.66 (found); % H, 6.81 (calc'd), 6.96 (found); % N, 4.98 (calc'd), 4.69 (found). $^1$H NMR Analysis: (d$_6$-DMSO): δ 12.0, s, 1H, 7.82-7.85, dd, 1H, 7.60-7.65, m, 1H, 7.33-7.36, dd, 1H, 7.06-7.11, m, 1H, 4.12-4.16, t, 2H, 2.15-2.27, t, 2H, 1.66-1.75, m, 2H, 1.28-1.54, m, 8H.

Compound 24: Melting point: 110-111° C. Combustion analysis: % C, 65.51 (calc'd), 65.47 (found); % H, 7.90 (calc'd), 7.73 (found); % N, 4.77 (calc'd), 4.65 (found). $^1$H NMR Analysis: (300 MHz, d$_6$-DMSO): δ 12.0, s, 1H, 8.9, s, 1H, 7.8, d, 1H, 7.08-6.99, m, 2H, 6.89-6.84, m, 1H, 3.99, t, 2H, 2.20, t, 2H, 2.07, s, 3H, 1.75, p, 2H, 1.56-1.30, m, 8H.

Compound 26: Melting point: 70-71.5° C. Combustion analysis: % C, 66.09 (calc'd), 65.92 (found); % H, 6.83 (calc'd), 6.67 (found). $^1$H NMR Analysis: (d$_6$-DMSO): δ 12.15, s, 1H, 7.56-7.45, m, 2H, 7.12, d, 1H, 7.00, t, 1H, 4.10, t, 2H, 2.92, q, 2H, 2.42, t, 2H, 2.00, p, 2H, 1.05, t, 3H.

Compound 27: Melting point: 68-69.5° C. Combustion analysis: % C, 68.16 (calc'd), 68.40 (found); % H, 7.63 (calc'd), 7.60 (found). $^1$H NMR Analysis: (d$_6$-DMSO): δ 12.0, s, 1H, 7.54-7.46, m, 2H, 7.13, d, 1H, 6.99, t, 1H, 4.08, t, 2H, 2.93, q, 2H, 2.24, t, 2H, 1.77, p, 2H, 1.47, m, 2H, 1.05, t, 3H.

Compound 28: Melting point: 85-86° C. Combustion analysis: % C, 69.84 (calc'd), 69.59 (found); % H, 8.27 (calc'd), 7.98 (found). $^1$H NMR Analysis: (d$_6$-DMSO): δ 12.0, s, 1H, 7.54-7.46, m, 2H, 7.13, d, 1H, 6.99, t, 1H, 4.08, t, 2H, 2.93, q, 2H, 2.20, t, 2H, 1.74, p, 2H, 1.52-1.30, m, 8H, 1.05, t, 3H.

Compound 29: Melting point: 67-69° C. Combustion analysis: % C, 71.22 (calc'd), 71.06 (found); % H, 8.81 (calc'd), 9.02 (found). $^1$H NMR Analysis: (d$_6$-DMSO): 12.0, s, 1H, 7.54-7.45 m, 2H, 7.12, d, 1H, 6.99, t, 1H, 4.06, t, 2H, 2.93, q, 2H, 2.18, t, 2H, 1.76, p, 2H, 1.51-1.36, m, 12H, 1.05, t, 3H.

Compound 32: Melting point: 89-92° C. Combustion analysis: % C, 64.27 (calc'd), 63.96 (found); % H, 7.19 (calc'd), 7.40 (found). $^1$H NMR Analysis: (d$_6$-DMSO): δ 12.2, broad s, 2H, 7.59, dd, 1H, 7.45, dt, 1H, 7.09, d, 1H, 6.97, t, 1H, 4.00, t, 2H, 2.20, t, 2H, 1.70, p, 2H, 1.54-1.27, m, 8H.

Compound 39: Melting point: 69-70.5° C. Combustion analysis: % C, 65.35 (calc'd), 65.39 (found); % H, 7.89 (calc'd), 7.80 (found). $^1$H NMR Analysis: (d$_6$-DMSO): δ

7.27, t, 1H, 6.67, d, 2H, 3.95, t, 2H, 3.73, s, 3H, 2.34, s, 3H, 2.18, t, 2H, 1.63, p, 2H, 1.49, p, 2H, 1.40-1.27, m, 6H.

Compounds 19, 21, 22, and 23 were also prepared by this method except that one equivalent of the appropriate alkylating agent, and two equivalents of potassium hydroxide were used, and the intermediate esters were purified by MPLC (Medium-Pressure Liquid Chromatography) using ethyl acetate and hexanes as the mobile phase. The following solvent compositions were used; 19 and 21 (20% ethyl acetate) and 22 and 23 (10% ethyl acetate).

Compound 19: Melting point: 58-59° C. Combustion analysis: % C, 66.91 (calc'd), 66.73 (found); % H, 8.42 (calc'd), 8.01 (found); % N, 5.57 (calc'd), 5.27 (found). $^1$H NMR Analysis: (d6-DMSO): δ 6.74-6.78, d, 1H, 6.60-6.68, m, 2H, 6.46-6.52, m, 1H, 3.88-3.93, t, 2H, 2.17-2.22, t, 2H, 1.66-1.76 (m, 2H, 1.30-1.56, m, 8H, Compound 21: Melting point: 115-117° C. Combustion analysis: % C, 63.14 (calc'd), 62.05 (found); % H, 7.23 (calc'd), 7.11 (found); % N, 6.69 (calc'd), 6.37 (found). $^1$H NMR Analysis: (d$_6$-DMSO): δ 6.74-6.77, dd, 1H, 6.60-6.68, m, 2H, 6.46-6.52, m, 1H, 3.90-3.94, t, 2H, 2.26-2.31, t, 2H, 1.63-1.78, m, 4H.

Compound 22: Melting point: 69-71° C. Combustion analysis: % C, 58.84 (calc'd), 58.84 (found); % H, 7.05 (calc'd), 7.08 (found); % N, 4.90 (calc'd), 4.83 (found). $^1$H NMR Analysis: (d$_6$-DMSO): δ 12.0, s, 1H, 6.72-6.74, d, 1H, 6.62-6.63, d, 1H, 6.44-6.48, dd, 1H, 5.0, s, 2H, 3.87-3.91, t, 2H, 2.17-2.22, t, 2H, 1.65-1.72, m, 2H, 1.28-1.52, m, 8H.

Compound 23: Melting point: 80-81° C. Combustion analysis: % C, 54.22 (calc'd), 54.15 (found); % H, 5.79 (calc'd), 5.74 (found); % N, 5.75 (calc'd), 5.66 (found). $^1$H NMR Analysis: (d$_6$-DMSO): δ 12.0, s, 1H, 6.72-6.75, d, 1H, 6.62-6.63, d, 1H, 6.45-6.49, dd, 1H, 5.0, br. s, 2H, 3.89-3.39, t, 2H, 2.25-2.30, t, 2H, 1.63-1.75, m, 4H.

Preparation of Compound 77

The general procedure for compound 12 was used to prepare the free acid form of compound 77 using the appropriate starting materials. The free acid of compound 77 (10.4 g, 38.43 mmole) was dissolved in ethanol (83.0 mL). A 10.0 N aqueous solution of sodium hydroxide (3.80 mL) was added, and the mixture was stirred at room temperature for approximately 2 hours. Ethanol was evaporated to yield a gel-like wet residue. The residue was dissolved in deionized water (200 mL) and extracted with ethyl acetate (2×100 mL). Residual ethyl acetate was removed by blowing nitrogen through the reaction vessel. The aqueous solution was then lyophilized to yield a white powder (6.50 g, 22.1 mmol, 58% yield). Melting point: >230° C. with decomposition. FARMS (pos.), m/z 295.2 (M+H)$^+$, 317.2 (M Na)$^+$. $^1$H NMR Analysis: (d$_6$-DMSO): δ 7.09-7.15, m, 3H, 4.05-4.09, t, 2H, 1.81-1.86, t, 2H, 1.58-1.68, m, 2H, 1.22-1.44, m, 8H.

Alternate Preparation of Compound 12

Potassium hydroxide (43.28 g, 771.3 mmol) was ground in a mortar until powdered, then added to a 500 mL Erlenmeyer flask containing 250 mL of dimethylsulfoxide. The resulting mixture was stirred for 15 minutes, after which time 27.47 g (201.8 mmol) of 2-hydroxyacetophenone was added, immediately followed by addition of 50.7 g (201.9 mmol) of ethyl 8-bromooctanoate. The reaction was stirred at room temperature for three hours. The cloudy, thick orange reaction mixture was poured into 150 mL of distilled water, and stirred until the solution became clear (about 15 minutes)

The clear orange solution was cooled to 0° C. in an ice bath, then acidified with concentrated aqueous hydrochloric acid until a solid formed (pH=7). The solid was collected by filtration and recrystallized from 50:50 ethanol:water to give 38.08 g (67.8%) of a yellow solid. Melting point: 72-73° C. Combustion analysis: % C, 69.04 (calc'd), 69.10 (found); % H, 7.97 (calc'd), 7.99 (found). $^1$H NMR Analysis: (d$_6$-DMSO): δ 12.0, s, 1H, 7.57, dd, 1H, 7.52, dt, 1H, 7.15, d, 1H, 7.00, dt, 1H, 4.09, t, 2H, 2.52, s, 3H, 2.20, t, 2H, 1.78, p, 2H, 1.46, m, 4H, 1.32, m, 4H.

Compound 54 was prepared by this method using the appropriate starting materials. The following compounds were also made by this method, replacing 2'-hydroxy-acetophenone with the compound listed in parentheses: 55 (2-hydroxy-5-methoxyacetophenone), 56 (2-hydroxy-4-methoxyacetophenone), and 58 (2-hydroxy-5-methylacetophenone).

Compound 54: Melting point: 71-73.5° C. Combustion analysis for $C_{18}H_{26}O_4 \cdot 0.068H_2O$: % C, 70.28 (calc'd), 69.98 (found); % H 8.56 (calc'd), 8.16 (found). $^1$H NMR Analysis: (300 MHz, d$_6$-DMSO): δ 11.8, s, 1H, 7.55, dd, 1H, 7.5, dt, 1H, 7.15, d, 1H, 7.0, dt, 1H, 4.1, t, 2H, 2.55, s, 3H, 2.2, t, 2H, 1.8, p, 2H, 1.5, m, 2H, 1.3, m, 10H.

Compound 55: Melting point: 120.5-121.5° C. Combustion analysis: % C, 66.21 (calc'd), 66.00 (found); % H 7.84 (calc'd), 7.54 (found). $^1$H NMR Analysis: (d$_6$-DMSO): δ 12.0, s, 1H, 7.1, m, 3H, 4.03, t, 2H, 3.72, s, 3H, 2.54, s, 3H, 2.20, q, 2H, 1.76, p, 2H, 1.53-1.30, m, 8H.

Compound 56: Melting point: 106-107.5° C. Combustion analysis: % C, 65.87 (calc'd), 65.76 (found); % H 7.86 (calc'd), 7.57 (found). $^1$H NMR Analysis: (d$_6$-DMSO): δ 7.65, d, 1H, 6.61-6.55, m, 2H, 4.08, t, 2H, 3.82, s, 3H, 2.49, s, 3H, 2.19, q, 2H, 1.78, p, 2H, 1.54-1.29, m, 8H.

Compound 58: Melting point: 121-123° C. Combustion analysis: % C, 68.16 (calc'd), 67.88 (found); % H 7.63 (calc'd), 7.65 (found). $^1$H NMR Analysis: (d$_6$-DMSO): δ 12.0, s, 1H, 7.37, m, 1H, 7.30, m, 1H, 7.04, d, 1H, 4.04, t, 2H, 2.52, s, 3H, 2.24, m, 5H, 1.76, p, 2H, 1.59-1.41, m, 4H.

Preparation of Compound 13

Compound 13 was purchased from Aldrich Chemical Co. (Milwaukee, Wis.).

Preparation of Compound 15

Potassium hydroxide (28.60 g, 0.511 mol) was ground up in a mortar and added to a 500 ml round bottom flask containing dimethyl sulfoxide (215 ml). This mixture was allowed to stir for 5 minutes. Phenol (12.00 g, 0.1277 mol) was added to the mixture. This was immediately followed by addition of ethyl 6-bromohexanoate (22.70 ml, 0.1277 mol). This mixture was allowed to stir for approximately 3 hours, at which time the reaction mixture was poured into 500 ml of water. The reaction mixture was then heated at 90° C. for 1.5 hours before heating was discontinued. This mixture was then allowed to stir overnight at room temperature. The reaction mixture was acidified with 2N aqueous hydrochloric acid and a white solid precipitated. The white solid was isolated by vacuum filtration and was allowed to dry overnight at room temperature in vacuo. 25.09 g (94.5% yield) of the product was recovered. Melting point: 64-67° C. Combustion analysis: % C, 69.23 (calc'd), 68.84 (found); % H, 7.69 (calc'd), 7.78 (found); % N, 0.00 (calc'd), <0.02 (found). $^1$H NMR Analysis: (300 MHz, d$_6$-DMSO): δ 11.95, s, 1H, δ 7.27, m, 2H, δ 6.90, m, 3H, 3.93, t, 2H, 2.20, t, 2H, 1.70, p, 2H, 1.50, p, 2H, 1.30, m, 6H.

Compounds 14, 16, 76, 75, and 68 were also prepared by this method using the appropriate starting materials.

Compound 14: Melting Point: 57-60° C. Combustion analysis: % C, 66.67 (calc'd), 66.49 (found); 6.67 (calc'd), 6.56 (found). $^1$H NMR Analysis: (300 MHz d$_6$-DMSO): δ 12.2 (s, 1H), 7.25 (m, 2H), 6.90 (m, 3H), 3.95 (t, 2H), 2.35 (t, 2H), 1.90 (p, 2H).

Compound 16: Melting point: 72-75° C. Combustion analysis: % C, 72.73 (calc'd), 72.45 (found); % H, 9.09 (calc'd), 8.92 (found). $^1$H NMR Analysis: (d$_6$-DMSO): δ 12.0, s, 1H, 7.24, t, 2H, 6.88, m, 3H, 3.89, t, 2H, 2.15, t, 2H, 1.35, m, 4H, 1.21, m, 8H.

Compound 75: Melting point: 55-57° C. Combustion analysis: % C, 62.26 (calc'd), 61.93 (found); % H 6.17 (calc'd), 5.89 (found); % F 8.95 (calc'd), 9.11 (found). $^1$H NMR Analysis: (d$_6$-DMSO): δ 7.25-7.10 m, 3H, 6.95-6.83, m, 1H, 4.05, t, 2H, 2.31, t, 2H, 1.77-1.62, m, 4H.

Compound 76. Melting point: 65-67° C. Combustion analysis: % C, 54.96 (calc'd), 54.62 (found); % H 5.0 (calc'd), 4.97 (found); % F 21.73 (calc'd), 21.73 (found). $^1$H NMR Analysis: (d$_6$-DMSO): δ 12.0, s, 1H, 7.61, d, 2H, 7.26, broad d, 1H, 7.10, broad t, 1H, 4.12, t, 2H, 2.31, t, 2H, 1.80-1.61, m, 4H.

Compound 68. Melting point: 67-68° C. Combustion analysis: % C, 62.11 (calc'd), 61.77 (found); % H 7.07 (calc'd), 6.94 (found); Cl 13.09 (calc'd) 13.05 (found). $^1$H NMR Analysis: (d$_6$-DMSO): δ 12.0, s, 1H, 7.32, t, 1H, 7.00-6.95, m, 2H, 6.91-6.88, m, 1H, 3.99, t, 2H, 2.23, t, 2H, 1.78, p, 2H, 1.62, p, 2H, 1.45-1.30, m, 6H.

Preparation of Compound 17

Compound 17 was purchased from Aldrich Chemical Co. (Milwaukee, Wis.).

Preparation of Compound 25

To a 250-mL round bottom flask were added, in turn, 5.57 g (33.9 mmol) of 2-hydroxycinnamic acid, 80 mL of methanol, and 6 drops of concentrated sulfuric acid. The resulting clear solution was heated to reflux for 6 hours and then allowed to cool to room temperature. The solvent was removed in vacuo to give a sticky white solid. The solid was dissolved in 80 mL of ethyl acetate, and washed with: 3 40-mL portions of 10% aqueous sodium bicarbonate; 1 40-mL portion of water; and 2 25 mL portions of brine. The organic layer was concentrated in vacuo to give 5.51 g (91.4%) of methyl 2-hydroxycinnamate as a white solid.

Potassium hydroxide (7.63 g, 136.0 mmol) was ground in a mortar until powdered, then added to a 125 mL Erlenmeyer flask containing 75 mL of dimethylsulfoxide. The resulting mixture was stirred for 10 minutes, after which time 5.49 g (30.8 mmol) of methyl 2-hydroxycinnamate and 7.81 g (31.1 mmol) of ethyl 8-bromooctanoate were added. The reaction was stirred at room temperature for about five hours, after which time 50 mL of distilled water were added. The yellow solution was stirred at room temperature overnight, then washed with 2 80 mL portions of ethyl acetate. The aqueous layer was cooled to 0° C. Concentrated aqueous hydrochloric acid was added until the pH of the solution was about 5. The resulting solid was collected by filtration and recrystallized from 50:50 (ethanol:water) to give 4.31 g (45.7%) of a white powder. Melting point: 148-150° C. Combustion analysis: % C, 66.65 (calc'd), 66.59 (found); % H, 7.24 (calc'd), 7.24 (found). $^1$H NMR Analysis: (300 MHz, d$_6$-DMSO): δ 12.0, broad s, 2H, δ 7.86, s, 7.81, s, 1H, 7.67-7.63, dd, 1H, 7.39-7.33, dt, 1H, 7.07-7.04, d, 1H, 6.98-6.93, t, 1H, 6.55, s, 6.50, s, 1H, 4.04, t, 2H, 2.19, t, 2H, 1.76, p, 2H, 1.50, m, 2H, 1.43-1.28, m, 6H.

Preparation of Compound 30

Salicylamide (5.3 g, 0.03875 mol) was added to a one-neck round bottom flask containing (15.0 g, 0.03875 mol) ethyl 8-bromooctanoate. Potassium carbonate (6.43 g, 0.0465 mol) was added in one portion and 35 ml of acetone was used as the solvent. The reaction was heated for approximately 4 hours. Heating was discontinued and the reaction was cooled to room temperature and allowed to stir over the weekend. HPLC indicated one peak at retention time 6.44 minutes, and the reaction was stopped. The reaction mixture was vacuum filtered, and the filter cake was washed with acetone. The filtrate was concentrated in vacuo to remove excess solvent (acetone).

The solids were stirred in hexanes for several hours, filtered, and then isolated and dried under vacuum overnight. The solids (10.93 g 0.0439 mol) were stirred in 1.5 eq. of 2N sodium hydroxide (32 ml, 0.0658 mol). The reaction was heated and stirred until completion as indicated by HPLC. The reaction was cooled to room temperature. An ice/water bath was placed around the reaction vessel and the slurry was acidified with 2N aqueous hydrochloric acid. The solids were recovered by vacuum filtration, and the filter cake was washed with water. The solids were dried under vacuum overnight, then transferred to an Erlenmeyer flask to be recrystallized using ethanol/water. Solids precipitated out overnight and were isolated and dried to give 8.08 g of 8-(2-carboxamidophenoxy)caprylic acid. Melting point: 114-116° C. Combustion analysis: % C, 64.51 (calc'd), 64.50 (found); % H, 7.52 (calc'd), 7.55 (found); % N, 5.02 (calc'd), 4.86 (found). $^1$H NMR Analysis: (d$_6$-DMSO): δ 12.0, s, 1H, 7.82, dd, 1H, 7.55, broad s, 2H, 7.45, dt, 1H, 7.12, d, 1H, 7.01, t, 1H, 4.10, t, 2H, 2.20, t, 2H, 1.77, p, 2H, 1.54-1.29, m, 8H.

Preparation of Compound 33

Preparation of N-ethylsalicylamide. Dimethylacetamide (50 ml) and carsalam (10.00 g, 0.0613 mol) were placed into a round bottom flask fitted with nitrogen purge, cold water condenser and a magnetic stir bar. Sodium carbonate (6.50 g, 0.0613 mol) and iodoethane (4.38 ml, 0.0548 mol) were added and heating of the reaction mixture was started. Heating at 80° C. continued for 16 hours at which point heating was discontinued and the reaction mixture was allowed to cool to room temperature. The reaction mixture was then filtered through a sintered glass funnel and the filtrate was collected. Water was added to this filtrate until a white solid precipitated. The solid was isolated by filtration and placed in an Erlenmeyer flask with 2N aqueous sodium hydroxide solution (200 ml). This mixture was heated at reflux for approximately 1 hour and then stirred overnight at room temperature. This mixture was acidified with 2N aqueous hydrochloric acid and a yellow oil was noted to separate out. The reaction mixture was extracted two times with 200 ml portions of ethyl acetate. The combined ethyl acetate layers were washed two times with 200 ml portions of deionized water, dried with sodium sulfate and concentrated under vacuum. N-ethylsalicylamide was recovered as a yellow oil which, after drying overnight under vacuum, was isolated in a yield of 7.93 g.

Preparation of O-acetyl-N-ethylsalicylamide. The N-ethylsalicylamide (7.93 g, 0.0481 mol), produced above, and methylene chloride (100 ml) were placed in a round bottom flask fitted with nitrogen purge, addition funnel and magnetic stir bar. This solution was cooled in an ice water bath and then triethylamine (14.71 ml, 0.1057 mol) was added. Acetyl chloride (3.76 g, 0.0529 mol) was placed into the addition funnel and slow dropwise addition over approximately 10 minutes was made to the reaction mixture. After 1 hour the ice water bath was removed and the reaction mixture was allowed to come to room temperature overnight. The reaction mixture was then diluted with dichloromethane (100 ml) and was extracted first with 100 ml of 2N aqueous hydrochloric acid and then with two 100-ml portions of deionized water. The methylene chloride layer was then dried with sodium sulfate and concentrated under vacuum. The resulting oil was then purified by elution through a silica gel column. A mixture of 60:40 hexane:ethyl acetate was used as the eluent, and 75 ml fractions were collected. Fractions containing the desired O-acetyl-N-ethyl-salicylamide were combined and concentrated under vacuum, yielding 4.28 g of the product as a yellow oil.

Preparation of 8-(2-(N-ethylbenzamide)oxy)octanoic acid. The above O-acetyl-N-ethylsalicylamide (4.28 g, 0.0207 mol) and dimethylformamide (75 ml) was added to a 250 ml round bottom flask fitted with nitrogen purge, addition funnel and magnetic stir bar. This mixture was cooled in an ice/water bath. After stirring for approximately 10 minutes, sodium hydride (0.76 g, 0.0316 mol) was added followed by dropwise addition of a solution of ethyl-8-bromooctanoate (7.78 g, 0.0310 mol) in dimethylformamide (25 ml) over a period of 25 minutes. The ice/water bath was then removed and the reaction mixture stirred overnight at room temperature. Deionized water (75 ml) was added to the reaction mixture, which was then extracted with three 75 ml portions of dichloromethane. The combined dichloromethane layers were then washed with three 75 ml portions of deionized water, dried with sodium sulfate, and concentrated under vacuum. The resulting brown oil was taken up in an aqueous sodium hydroxide solution (2N, 200 ml), heated at reflux for approximately 2 hours, and then allowed to cool to room temperature overnight. The mixture was acidified with 2N aqueous hydrochloric acid and extracted with three 100-ml portions of ethyl acetate. The combined ethyl acetate layers were washed with three 100 ml portions of deionized water and then with three 100 ml portions of brine solution. The ethyl acetate layer was dried with sodium sulfate, and concentrated under vacuum. The resulting oil was then crystallized from an ethyl acetate:hexane 30:70 mixture yielding 3.24 g of the desired product, 8-(2-(N-ethylbenzamide)oxy) octanoic acid. Melting Point: 94-95° C. Combustion Analysis: % C, 67.29 (calc.), 67.18 (found); % H, 8.41 (calc.), 8.55 (found); % N, 4.36 (calc.), 4.26 (found). $^1$H NMR Analysis: ($d_6$-DMSO): δ 12.0 s, 1H, 7.93, d, 1H, 7.75, dd, 1H, 7.40, td, 1H, 7.10, d, 1H, 6.98, td, 1H, 4.00, m, 3H, 2.15, t, 2H, 1.71, p, 2H, 1.25, m, 8H, 1.10, d, 6H.

Compounds 31 and 34 were also prepared by this method using the appropriate starting material.

Compound 31. Melting point: 91.5-94° C. Combustion analysis: % C, 65.51 (calc'd), 65.35 (found); % H, 7.90 (calc'd), 8.03 (found); % N, 4.77 (calc'd), 4.46 (found). $^1$H NMR Analysis: (300 MHz, $d_6$-DMSO): δ 12.0, s, 1H, 8.02, broad d, 1H, 7.72, dd, 1H, 7.42, dt, 1H, 7.11, d, 1H, 7.00, t, 1H, 4.08, t, 2H, 2.80, d, 3H, 2.20, t, 2H, 1.77, p, 2H, 1.53-1.25, m, 8H.

Compound 34: Melting Point: 94-95° C. Combustion Analysis: % C, 67.29 (calc'd), 67.18 (found); 8.41 (calc'd), 8.55 (found); % N, 4.36 (calc'd), 4.26 (found). $^1$H NMR Analysis: ($d_6$-DMSO): δ 12.0 (s, 1H), 7.93 (d, 1H), 7.75 (dd, 1H), 7.40 (td, 1H), 7.10 (d, 1H), 6.98 (td, 1H), 4.00 (m, 3H), 2.15 (t, 2H), 1.71 (p, 2H), 1.25 (m, 8H), 1.10 (d, 6H).

Preparation of Compound 36

To a 250 mL round bottom flask fitted with a condenser were added 5.00 g (17.4 mmol) of compound 12 and 170 mL of ethanol. The flask was flushed with nitrogen. Sodium borohydride (1.15 g, 30.4 mmol) was added to the clear, yellow solution of compound 12 in three portions. The reaction mixture was stirred for two hours, then checked by HPLC for completion. An additional 0.38 g (10.0 mmol) of sodium borohydride was added, and the reaction mixture stirred at room temperature overnight. The reaction was quenched by the addition of 30 mL of 10% aqueous sodium bicarbonate, then filtered through a celite pad. The filtrate was concentrated in vacuo to give a pale yellow gel. The gel was stirred in 60 mL of 1N aqueous sodium hydroxide for two hours, cooled to 0° C., then acidified to pH=1 with concentrated aqueous hydrochloric acid. The aqueous layer was extracted with four 30 mL portions of ethyl acetate. The combined organic layers were dried over sodium sulfate and concentrated in vacuo to give 2.46 g (48.8%) of product as a clear, viscous yellow oil. Combustion analysis: % C, 67.51 (calc'd), 67.16 (found); % H, 8.67 (calc'd), 8.56 (found). (Note that combustion analysis includes 0.176 mol $H_2O$ (from KF value) and 0.068 mol ethyl acetate (shown in NMR)). $^1$H NMR Analysis: (300 MHz, $d_6$-DMSO): δ 7.45-7.42, dd, 1H, 7.18-7.12, dt, 1H, 6.93-6.88, t, 2H, 5.03-4.97, 1H, 3.99-3.91, m, 2H, 2.20, t, 2H, 1.72, p, 2H, 1.51, m, 2H, 1.39-1.30, m, 6H, 1.27-1.25, d, 3H.

Preparation of Compound 37

A solution of 10.0 ml (11.31 g, 83.1 mmol) of 2'-hydroxyacetophenone and 50 ml of tetrahydrofuran was placed in an ice bath and treated with 120.0 ml (168.0 mmol) of 1.4M methyllithium in tetrahydrofuran, which was added dropwise over 30 minutes. The reaction mixture first became cloudy and then cleared up. After stirring for 18 hours, the solution was acidified with 4% aqueous hydrochloric acid. The layers were separated. The organic phase was washed with 30 ml of brine, dried over sodium sulfate, and concentrated. A total of 12.05 g of 2-(dimethylhydroxymethyl)phenol was isolated.

A solution of 6.77 g (44.5 mmol) of 2-(dimethylhydroxymethyl)phenol and 50 ml of dimethylsulfoxide was prepared and treated with 9.90 g (176 mmol) of freshly ground potassium hydroxide. The light green solution was stirred for 20 minutes, before 9.85 g (45.8 mmol) of 4-(bromomethyl)benzoic acid and 0.40 g (2.67 mmol) of sodium iodide were added. The thick slurry was stirred for 4 hours, after which another 1.66 g (7.72 mmol) of 4-(bromomethyl)benzoic acid was added. After stirring another 2 hours, the reaction mixture was treated with 50 ml of water. After stirring for 20 hours, the solution was acidified with 4% aqueous hydrochloric acid, giving a white solid, which was isolated by filtration. The solid was recrystallized from ethanol/water to yield 5.8 g of product. Melting point: 171-2° C. Combustion analysis: % C, 71.31 (calc'd), 71.28 (found); % H, 6.34 (calc'd), 6.14 (found). $^1$H NMR Analysis: (300 MHz, $d_6$-DMSO): δ 13.0, s, 1H, 8.0, d, 2H, 7.7, dd, 1H, 7.6, d, 2H, 7.2, dt, 1H, 7.1, d, 1H, 7.0, t, 1H, 5.25, s, 2H, 5.0, s, 1H, 1.55, s, 6H.

Preparation of Compound 67

A solution of 50.1 g (455 mmol) of hydroquinone, 15.52 g (91.0 mmol) of α-chloro-p-toluoylic acid, 1 g (6.7 mmol) of sodium iodide, 75 ml (750 mmol) of 10N aqueous sodium hydroxide and 300 ml of water was heated to 70° C. for 24 hours under a nitrogen atmosphere. The cooled reaction mixture was acidified with 20% aqueous hydrochloric acid, causing brown solids to develop. These solids were isolated by filtration. The solids were taken up in ethyl acetate. The undissolved solids were filtered off. The filtrate was washed with brine, dried over sodium sulfate and concentrated. The residue was crystallized from ethanol/water to give 8.1 g of Compound 67, melting point >230° C. Combustion analysis: % C, 68.85 (calc'd), 68.44 (found); % H, 4.95 (calc'd), 4.93 (found); $^1$H NMR Analysis: (d6-DMSO): δ 9.0, s, 1H, 8.0, d, 2H, 7.5, d, 2H 6.8, d, 2H, 6.7, d, 2H, 5.1, s, 2H.

Compounds 78 and 73 were prepared in the same manner as compound 67 using the appropriate starting materials.

Compound 78. Melting point: 178-81° C. Combustion analysis: % C, 64.01 (calc'd), 63.95 (found); % H, 4.22 (calc'd), 4.25 (found); $^1$H NMR Analysis: (d6-DMSO): δ 8.0, d, 2H, 7.6, d, 2H, 7.45, dd, 1H, 7.3, dt, 1H, 7.2, dd, 1H, 7.0, dt, 1H, 5.3, s, 2H.

Compound 73. Melting point: 63-65° C. Combustion analysis: % C, 62.11 (calc'd), 62.02 (found); % H, 7.07 (calc'd), 7.04 (found); $^1$H NMR Analysis: ($d_6$-DMSO): δ 12.0, bs, 1H, 7.4, dd, 1H, 7.3, dt, 1H, 7.1, dd, 1H, 6.95, dt, 1H, 4.0, t, 2H, 2.2, t, 2H, 1.75, p, 2H, 1.5, m, 4H, δ 1.35, m, 4H.

Preparation of Compound 60

A solution of 3.0 ml (3.44 g, 28.2 mmol) salicylaldehyde, 5.05 ml (6.33 g, 28.4 mmol) ethyl 6-bromohexanoate, and 50 ml ethanol was treated with 5.07 g (36.7 mmol) of potassium carbonate. The slurry was heated to reflux. After 20 hours, the reaction mixture was cooled to 25° C., filtered through a Celite pad and concentrated. The residue was rinsed with hexanes and then taken up in ethanol and 10 ml of 2N aqueous sodium hydroxide. After 6 hours the ethanol was stripped off. The mixture was acidified with 4% aqueous hydrochloric acid and extracted with ethyl acetate. The organic phase was washed with 30 ml of brine, dried over sodium sulfate, and concentrated. Recrystallization from ethanol/water gave 3.0 g of compound 60 as a brown solid. Melting point: 58-60° C. Combustion analysis: % C, 66.09 (calc'd), 61.39 (found); % H, 6.83 (calc'd), 6.98 (found). MS 236 (M+ peak). $^1$H NMR Analysis: ($d_6$-DMSO): δ 12.0, bs, 1H, 10.4, s, 1H, 7.7, dd, 1H, 7.65, dt, 1H, 7.2, d, 1H, 7.05 1.5, m, 2H.

Compound 61 was prepared in the same manner as Compound 60 using the appropriate starting materials. Melting point: 59-62° C. Combustion analysis: % C, 68.18 (calc'd), 67.59 (found); % H, 7.57 (calc'd), 7.63 (found). MS 264 (M+ peak). $^1$H NMR Analysis: ($d_6$-DMSO): δ 12.0, bs, 1H 10.4, s, 1H, 8.0, d, 2H, 7.75, dd, 1H, 7.65, dt, 2H, 7.3, d, 1H, 7.1, t, 1H, 5.4, s, 2H.

Preparation of Compound 51

Carsalam (30.00 g, 0.1840 mol), iodomethane (10.23 ml, 0.1643 mol), sodium carbonate (19.51 g, 0.1840 mol) and dimethylformamide (150 ml) were placed in a 500 ml round bottom flask. The reaction mixture was heated overnight at 80° C. After cooling to room temperature, the reaction mixture was filtered and a white solid collected. This was washed with water and the remaining solid placed into a 250 ml round bottom flask. Water was added to the filtrate from the initial filtration and more, white solid precipitated. This material was combined with the solid already in the 250 ml flask and 2N aqueous sodium hydroxide (150 ml) was added. The mixture was heated for one hour before heating was discontinued and the reaction mixture was allowed to cool overnight. Overnight, a white solid precipitated and was isolated by filtration and allowed to dry in vacuo. 21.52 g of N-methylsalicylamide was isolated.

N-methylsalicylamide (21.52 g, 0.1425 mol) and methylene chloride (300 ml) were placed in a one liter round bottom flask. The flask was cooled in an ice/water bath and triethylamine (43.62 ml, 0.3135 mol) was added. Dropwise addition of acetyl chloride was then made over a period of five minutes. The ice/water bath was then removed and the reaction mixture stirred overnight at ambient temperature. Methylene chloride (300 ml) was added to the reaction mixture. The mixture was washed with 2, 300 ml portions of 1N aqueous hydrochloric acid solution, and then with 3, 300 ml portions of deionized water. The methylene chloride solution was dried with sodium sulfate and concentrated in vacuo to yield an orange solid which was recrystallized from 70:30 ethyl (acetate:hexane). 12.15 g of the O-acetyl,N-methyl salicylamide was isolated.

O-acetyl,N-methyl salicylamide (17.74 g, 0.919 mol), which was prepared as described above, was placed in a one liter round bottom flask with dimethylformamide (300 ml). The flask was cooled in an ice/water bath and sodium hydride (3.38 g, 0.1406 mol) was added. Methyl 8-bromodecanoate (36.54 g, 0.1379 mol) was dissolved in an additional portion of dimethylformamide (100 ml) and this solution was added dropwise to the reaction mixture over a period of 25 minutes. After stirring for about a half hour the ice bath was removed, and the reaction mixture was allowed to stir for three days at ambient temperature. Water (300 ml) was added, and this mixture was extracted with two, 250 ml portions of methylene chloride. The combined methylene chloride layers were then washed three times with 150 ml portions of water, dried with sodium sulfate and concentrated in vacuo yielding a brown oil. This oil was then taken up in a 2N aqueous sodium hydroxide solution (200 ml) and heated for 45 minutes. After stirring overnight at ambient temperature, an additional 200 ml of 2N aqueous sodium hydroxide was added, and the reaction mixture was heated until it cleared. After cooling, the reaction mixture was acidified with a 2N aqueous hydrochloric acid solution and extracted with 3, 250 ml portions of ethyl acetate. The combined ethyl acetate layers were washed with 3, 250 ml portions of water, and then with 3, 250 ml portions of brine. The ethyl acetate layer was dried with sodium sulfate and concentrated in vacuo, yielding a tan solid which was recrystallized from 30:70 (ethyl acetate:hexane). The product was isolated as a white solid in a yield of 26.30 g. Compound 51 analytical data: Melting point: 81-84° C. Combustion analysis: % C, 67.29 (calc'd), 67.17 (found); % H 8.41 (calc'd), 8.70 (found); % N, 4.36 (calc'd), 4.36 (found). $^1$H NMR Analysis: ($d_6$-DMSO): δ 12.00, s, 1H, 7.98, d, 1H, 7.70-7.75, dd, 1H, 7.39-7.48, dt, 1H, 7.09-7.15, d, 1H, 6.95-7.05, td, 1H, 4.05, t, 2H, 2.75, d, 3H, 2.15, t, 2H, 1.70, p, 2H, 1.20-1.55, m, 12H.

Preparation of Compound 65

Potassium hydroxide (28.60 g, 0.511 mol) was placed in a 500 ml round bottom flask. Dimethylsulfoxide (215 ml) was added and stirring started. After stirring for about 35 minutes, phenol (12.00 g, 0.1277 mol) was added followed by addition of ethyl 8-bromoocatanoate (32.04 g, 0.1277 mol). This mixture was allowed to stir at ambient temperature for 3 hours and 500 ml of deionized water was added. This mixture was heated at reflux. The reaction mixture was cooled to room temperature and acidified with 2N aqueous hydrochloric acid solution. The resulting white solid was isolated by filtration and was allowed to dry in vacuo overnight. 27.74 g of 8-phenoxyoctanoic acid was recovered. Compound 65 analytical data: Melting point: 65-68° C. Combustion analysis: % C, 71.19 (calc'd), 70.98 (found); % H 8.47 (calc'd), 8.70 (found). $^1$H NMR Analysis: ($d_6$-DMSO): δ 11.95, s, 1H, 7.23-7.31, m, 2H, 6.87-6.95, m, 3H, 3.90, t, 2H, 2.15, t, 2H, 1.62, p, 2H, 1.45, p, 2H, 1.22-1.45, m, 6H.

Preparation of Compound 43

Potassium hydroxide (2.62 g, 0.0467 mol) and dimethyl sulfoxide (90 ml) were placed in a 500 ml round bottom flask under nitrogen. After stirring for 5 minutes, resorcinol monobenzoate (10.0 g, 0.0467 mol) was added followed by ethyl 8-bromooctanoate (11.73 g, 0.0467 mol). After stirring overnight at room temperature, an additional portion of potassium hydroxide (2.62 g, 0.0467 mol) was added to the mixture in an effort to get the reaction to go to completion. After stirring for an additional 5.5 hours, water (200 ml) was added to the mixture, which was then extracted with three portions of dichloromethane (100 ml portions). The combined dichloromethane portions were dried with sodium sulfate and concentrated in vacuo. The resulting brown oil was noted to have an odor of dimethyl sulfoxide and was taken up in water. This mixture was then extracted with three portions of ethyl acetate (100 ml portions). The combined ethyl acetate layers were then washed with three portions of water (100 ml portions). The ethyl acetate layer was dried with sodium sulfate and was concentrated in vacuo. The resulting brown oil was taken up in an aqueous sodium hydroxide solution (2N, 100 ml). Tetrahydrofuran (50 ml) was then added and the mixture was heated to reflux for 2 hours before heating was discontinued. Tetrahydrofuran was removed in vacuo, and the reaction mixture was acidified with 2N aqueous hydrochloric acid. The resulting tan solid was washed several times in 40-50° C. water, and then was recrystallized from 80:20 (water:ethanol). The resulting tan solid was recrystallized first from 90:10 (hexane:ethyl acetate) and then was added to boiling water. Ethyl alcohol was added until the mixture cleared. Upon cooling a tan solid precipitated and was isolated by filtration. This product was allowed to dry in vacuo and was isolated in a yield of 5.96 g. Compound 43 analytical data: Melting point=89-91° C. Combustion Analysis: % C, 66.67 (calc'd), 66.68 (found) % H, 7.94 (calc'd), 7.92 (found). $^1$H NMR Analysis: ($d_6$-DMSO): δ 12.0, s, 1H, 9.3, s, 1H, 7.00, t, 1H, 6.29, m, 3H, 3.84, t, 2H, 2.15, t, 2H, 1.62, p, 2H, 1.45, p, 2H, 1.23, m, 6H.

Compounds 44, 45, 74, and 46 were made by the above method using the appropriate starting material:

Compound 44: Melting Point: 89-92° C. Combustion Analysis: % C, 68.57 (calc'd), 68.71 (found); % H, 8.57 (calc'd), 8.58 (found). $^1$H NMR Analysis: ($d_6$-DMSO): δ 11.9, s, 1H, 9.2, s, 1H, 7.00, t, 1H, 6.29, m, 3H, 3.84, t, 2H, 2.15, t, 2H, 1.62, p, 2H, 1.30, p, 2H, 1.23, m, 8H.

Compound 45: Melting Point: 98-99.5° C. Combustion Analysis: % C, 64.29 (calc'd), 64.06 (found); % H, 7.14 (calc'd), 7.12 (found). $^1$H NMR Analysis: ($d_6$-DMSO): δ 12.0, s, 1H, 9.3, s, 1H, 7.00, t, 1H, 6.29, m, 3H, 3.84, t, 2H, 2.17, t, 2H, 1.62, p, 2H, 1.49, p, 2H, 1.35, m, 2H.

Compound 74: Melting Point: 126-128° C. Combustion Analysis: % C, 56.57 (calc'd), 56.72 (found); 6.39 (found), 6.66 (found); % N, 4.71 (calc'd), 4.32 (found). $^1$H NMR Analysis: ($d_6$-DMSO): δ 11.7, s, 1H, 10.4, s, 1H, 7.75-7.8, dd, 1H, 7.68-7.73, d, 1H, 6.92-6.99, d, 1H, 4.00, t, 2H, 2.15, t, 2H, 1.67, p, 2H, 1.22-1.55, m, 8H.

Compound 46: Melting Point=93-95° C. Combustion Analysis: % C, 61.22 (calc'd), 61.20 (found); % H, 6.12 (calc'd), 6.02 (found). $^1$H NMR Analysis: ($d_6$-DMSO): δ 12.0, s, 1H, 9.3, s, 1H, 7.01, t, 1H, 6.30, m, 3H, 3.86, t, 2H, 2.35, t, 2H, 1.85, p, 2H.

Preparation of Compound 47

Potassium hydroxide (11.20 g, 200.0 mmol) was ground in a mortar until powdered, then added to a 0.5 L round bottom flask containing 90 mL of dimethyl sulfoxide. The resulting mixture was stirred for 5 minutes, after which time 10.00 g (50.0 mmol) of 4-benzyloxyphenol were added immediately followed by 12.55 g (50.0 mmol) of ethyl 8-bromooctanoate. The reaction was stirred at room temperature for two and one half hours. The reaction mixture was poured into 200 mL of distilled water. The mixture was heated to reflux. When the reaction completed, the reaction mixture was allowed to cool to room temperature. The mixture was acidified with 2N aqueous hydrochloric acid solution and the resulting solid was isolated by filtration. The solid was allowed to dry under vacuum overnight. 17.96 g of the (4-benzyloxyphenyl)-8-oxyoctanoic acid was isolated. This material was used as is for the next step.

The (4-benzyloxyphenyl)8-oxyoctanoic acid was placed into a 0.5 L round bottomed flask with 120 ml of ethyl alcohol. The mixture was sparged for 15 minutes with nitrogen before 10% palladium on activated carbon was added to the reaction mixture. The flask was then evacuated, and a balloon containing hydrogen was placed atop the flask such that the contents of the flask were kept under a hydrogen atmosphere. The mixture was allowed to stir overnight at room temperature, and was then filtered through Celite. Ethyl alcohol was removed in vacuo, yielding a white solid which was first recrystallized from 90:10 ethyl alcohol: water and then was dissolved in 2N aqueous sodium hydroxide. The mixture was filtered and acidified with 2N aqueous hydrochloric acid. The resulting white solid was isolated by filtration and allowed to dry under vacuum. 2.12 g of the (4-hydroxyphenyl)-8-oxyoctanoic acid was isolated. Compound 47 analytical data: Melting point: 97-100° C. Combustion analysis: % C, 66.67 (calc'd), 66.43 (found); % H, 7.94 (calc'd), 7.80 (found). $^1$H NMR Analysis: ($d_6$-DMSO): δ 12.0, s, 1H, 9.00, s, 1H, 6.63, m, 4H, 3.75, t, 2H, 2.15, t, 2H, 1.60, p, 2H, 1.45, p, 2H, 1.20, m, 6H.

Compounds 48, 49, and 50 were made by the above method using the appropriate starting material:

Compound 48: Melting point: 99-100° C. Combustion analysis: % C, 68.57 (calc'd), 68.47 (found): % H, 8.57 (calc'd), 8.67 (found). $^1$H NMR Analysis: ($d_6$-DMSO): δ 6.63, m, 4H, 3.75, t, 2H, 2.15, t, 2H, 1.60, p, 2H, 1.45, p, 2H, 1.20, m, 10H.

Compound 49: Melting point: 102-104° C. Combustion analysis: % C, 64.29 (calc'd), 64.53 (found); % H, 7.14 (calc'd), 7.32 (found). $^1$H NMR Analysis: ($d_6$-DMSO): δ 11.5, s, 1H, 8.5, s, 1H, 6.63, m, 4H, 3.75, t, 2H, 2.15, t, 2H, 1.60, p, 2H, 1.45, p, 2H, 1.30, m, 2H.

Compound 50: Melting point: 117-120° C. Combustion analysis: % C, 58.43 (calc'd), 58.63 (found); % H, 6.35 (calc'd), 6.40 (found). $^1$H NMR Analysis: ($d_6$-DMSO): δ 12.0, s, 1H, 8.6, s, 1H, 6.62, m, 4H, 3.80, t, 2H, 2.50, t, 2H, 1.80, p, 2H.

Preparation of Compound 57

2,5-dihydroxyacetophenone (5.00 g, 0.0329 mol), benzyl bromide (3.72 ml, 0.031 mol), potassium carbonate (4.31 g, 0.031 mol) and acetone (150 ml) were added to a 500 ml round bottom flask. The reaction mixture was heated overnight at reflux and then was cooled to ambient temperature. When cool, deionized water (150 ml) was added to the reaction mixture and the reaction mixture was extracted three times with 100 ml portions of diethyl ether. The combined ether layers were dried with sodium sulfate and concentrated in vacuo yielding a dark solid. This dark solid was recrystallized from 50:50 (ethanol:water) yielding 3.09 g of 2-hydroxy-5-benzyloxyacetophenone as yellow needles.

Potassium hydroxide (11.11 g, 0.1983 mol) and dimethyl sulfoxide (90 ml) were added to a 250 ml round bottom flask. After 10 minutes, 2-hydroxy-5-benzyloxyacetophenone (12.00 g, 0.0496 mol), prepared as outlined above, was added followed by addition of ethyl 8-bromoocatanoate (12.45 g, 0.496 mol). The reaction mixture was stirred overnight at ambient temperature. Deionized water was added and the reaction mixture was heated at reflux for five hours. At the end of this period, the reaction mixture was allowed to come to room temperature, and was acidified with a 2N aqueous hydrochloric acid solution. The resulting tan solid was isolated by filtration and was washed two times with portions of deionized water. After drying overnight in vacuo, 16.75 g of the (4-benzyloxy-2-acetylphenyl)-8-oxyoctanoic acid was recovered.

(4-benzyloxy-2-acetylphenyl)-8-oxyoctanoic acid (16.75 g, 0.0435 mol) and ethyl acetate (85 ml) were placed in a 300 ml Parr reactor. 10% palladium on activated carbon (0.75 g) was added and the reactor was sealed, evacuated, and charged with hydrogen. After the reactor was heated at 50° C. overnight, the reactor was opened and an additional 0.5 g of 10% palladium on activated carbon was added. The reactor was again sealed, evacuated and charged with hydrogen. When no change in the reaction mixture had occurred after two days at ambient temperature, the reactor was again opened and the reaction mixture was filtered. The filtrate was concentrated in vacuo and the residue was placed in the Parr reactor once again. The residue was then taken up in ethyl acetate, and 10% palladium on activated carbon was added. The reactor was sealed, evacuated, charged with hydrogen and heated overnight at 50° C. After cooling to ambient temperature, the reactor was opened, the palladium on activated carbon was filtered off, and the reaction mixture was concentrated in vacuo. The resulting yellow solid was recrystallized from 80:20 water:ethyl alcohol. The yellow solid resulting from this recrystallization was taken up in boiling hexane. Ethyl acetate was then added until a clear solution was achieved, and the mixture was allowed to cool to room temperature. A tan solid, which precipitated, was isolated by filtration and dried in vacuo. 6.23 g of (4-hydroxy-2-acetylphenyl)-8-oxyoctanoic acid was recovered. Compound 57 analytical data: Melting point: 112-115° C. Combustion analysis: % C, 65.31 (calc'd), 65.32 (found); % H 7.48 (calc'd), 7.39 (found). $^1$H NMR Analysis: (d$_6$-DMSO): δ 6.88-7.02, m, 3H, 3.92, t, 2H, 2.49, s, 3H, 2.15, t, 2H, 1.69, p, 2H, 1.20-1.59, m, 8H.

Preparation of Compound 81

Preparation of 8-(4-benzyloxy-phenoxy)-2-methyl octanoic acid, ethyl ester—

Airless techniques were used during the transfer of liquids. 14.0 grams of 8-(4-benzyloxy-phenoxy)octanoic acid, ethyl ester (0.03778 mol., 1 eq.) was added to a flame dried 250 mL 3-necked round-bottomed flask containing a stirbar. To this was added 80 mL of anhydrous THF. The mixture was stirred for 10 minutes or until the solid was completely dissolved. The mixture was cooled to −78° C. using dry ice and an acetone bath. To the mixture was added 19.84 mL of a 2M lithium diisopropylamide solution (0.03967 mol., 1.05 eq.). The addition was done slowly to maintain a temperature below −60° C. After the addition was complete the mixture was allowed to stir for 2.0 hours at −78° C. upon which time the suspension was slowly quenched with 4.70 mL of iodomethane (0.07556 mol., 2.0 eq.). The temperature was not allowed to increase above −50° C. during the addition. The reaction was allowed to slowly warm to room temperature and stir over 3 days. The solution was filtered away from preciptates and the supernatant reduced to a residue in vacuo. The residue was taken up in 60 mL of ethyl acetate and was with satd. Sodium bicarbonate solution (50 mL) and satd. NaCl solution (50 mL). The ethyl acetate layer was then dried with 4.5 grams of anhydrous sodium sulfate and filtered. The organic layer was reduced to a residue "in vacuo". The final product was golden oil with a final raw yield of 9.10 grams (62.6% yield). HPLC indicated that that small amounts of the starting material remained along with some dimethylated by-product. This intermediate product was not characterized and was used as is in the next step.

The compound was debenzylated with Pd/C and H$_2$ as described in preparation of compound 47. The resulting product was hydrolyzed according to methods described for compound 47 to produce the compound 81.

Yield was 67.85%. Product was a white solid. M.P. was 67°-70° C. Elemental Analysis: Theoretical C=67.65%, H=8.330. Found C=67.56%, H=8.56%; Quantitative $^{13}$C-NMR (d$_6$-DMSO): C=O (1C, 177.477); C$_{Ar}$—O (2C, 151.467 & 151.015 ppm); C$_{Ar}$—H (4C, 115.617 & 115.209 ppm); CH$_2$—CH$_2$—O (1C, 67.939 ppm); CH—CH$_3$ (1C, 38.689 ppm); =CH$_2$— (5C, 33.211, 28.769, 26.645, 25.451 ppm.); CH—CH$\overline{3}$ (1C, 16.944 ppm)

Preparation of Compound 82

Preparation of 8-(4-benzyloxy-phenoxy)-2-(propen-2-yl)octanoic acid, ethyl ester Airless techniques were used during the transfer of liquids. 10.0 grams of 8-(4-benzyloxy-phenoxy)octanoic acid, ethyl ester (0.02699 mol., 1 eq.) was added to a flame dried 250 mL 3-necked round-bottomed flask containing a stirbar. To this was added 100 mL of anhydrous THF. The mixture was stirred for 10 minutes or until the solid was completely dissolved. The mixture was cooled to −78° C. using a dry ice and acetone bath. To the mixture was added 24.0 mL of a 2M lithium diisopropylamide solution (0.0480 mol., 1.7 eq.). The addition was done slowly to maintain a temperature below −60° C. After the addition was complete the mixture was allowed to stir for 2.0 hours at −78° C. upon which time the suspension was slowly quenched with 5.0 mL of allyl bromide (0.0577 mol., 2.13 eq.). The temperature was not allowed to increase above −50° C. during the addition. The reaction was allowed to slowly warm to room temperature and stir over 16 hours. The solution was filtered away from preciptates and the supernatant reduced to a residue "in vacuo". The residue was taken up in 60 mL of ethyl acetate and was with satd. Sodium bicarbonate solution (50 mL) and satd. NaCl solution (50 mL). The ethyl acetate layer was then dried with 4.5 grams of anhydrous sodium sulfate and filtered. The organic layer was reduced to an oil and chromatographed on silica gel using (9:1) hexanes to ethyl acetate. The final product was golden oil with a final yield of 7.0 grams (64.1% yield). Quantitative $^{13}$C-NMR (d-CDCl$_3$): C=O (1C, 175.462 ppm); C$_{Bn}$ (6C, 137,188, 128.36, 127.679, 127.298 ppm) C$_{Ar}$—O (2C, 153.303 & 152.683 ppm); C$_{Ar}$—H (4C, 115.607 & 115.176 ppm); =CH$_2$ (1C, 116.484 ppm); ( $\underline{CH_2})_{Bn}$ (1C, 70.439 ppm); ($\underline{CH_2}$—CH$_2$—O (1C, 68.242 ppm); CH$_3$—$\underline{CH_2}$—O (1C, 59.946 ppm); CH—$\underline{CH_3}$ (1C, 45.147 ppm); —$\underline{CH2}$-CH= (1C, 36.404 ppm); —$\underline{CH_2}$— (5C, 31.609, 29.121, 27.054, 25.745 ppm.); CH$_2$—$\underline{CH_3}$ (1C, 14.221 ppm).

The compound was debenzylated with Pd/C and H$_2$ as described in preparation of compound 47. The resulting product was hydrolyzed according to methods described for compound 47 to produce the compound 82. Yield was 67.66%. Product was a white solid. M.P. was 98°-100° C. Elemental Analysis: Theoretical C=69.36%, H=8.90%. Found C=69.33%, H=8.96%; Quantitative $^{13}$C-NMR (d$_6$-DMSO): $\underline{C}$=O (1C, 177.226); $\underline{C}_{Ar}$—O (2C, 151.660 & 151.216 ppm); $\underline{C}_{Ar}$—H (4C, 115.786 & 115.368 ppm); $\underline{CH_2}$—CH$_2$—O (1C, 67.908 ppm); CH—$\underline{CH_2}$ (1C, 44.887 ppm); —$\underline{CH_2}$— (5C, 34.341, 28.968, 27.071, 25.614 ppm.); CH=$\underline{CH_2}$ (1C, 32.060 ppm); CH$_2$—$\underline{CH3}$ (1C, 20.312 ppm); $\underline{CH_2}$—CH3 (1C, 14.007 ppm)

Preparation of Compound 80

Preparation of 8-(4-methoxy-phenoxy)octanoic acid, ethyl ester

To a 500 mL 3-necked round bottomed flask was added 14.90 grams of 4-methoxyphenol (0.12 mol.), 30.0 grams of 8-bromo ethyloctanoate (0.1265 mol.), 10.36 grams of potassium carbonate (0.075 mol.), 150 mL of dry acetone, and 2.5 mole % of potassium iodide. The reaction was kept under nitrogen and refluxed for 2 days. The heterogeneous mixture was evaporated "in vacuo" to a solid residue and mixed with 600 mL of equal parts of water and ethyl acetate. The two phases were separated and the organic layer extracted with 3N NaOH solution (3×150 ml). The organic layer was again extracted once with satd. NaCl solution. The organic layer was dried over anhydrous magnesium sulfate and filtered. The organic solution was then reduced to half volume (~180 mL) and topped with an equal amount of hexane. This was placed in a refrigerator overnight. The crystals that formed were vacuum filtered and allowed to air dry. The product was not further analyzed and was used "as is" in the following steps.

Preparation of 8-(4-methoxy-phenoxy)-2-methyl octanoic acid, ethyl ester

Airless techniques were used during the transfer of liquids. 14.0 grams of the compounds produced above (0.03778 mol., 1 eq.) was added to a flame dried 250 mL 3-necked round-bottomed flask containing a stirbar. To this was added 80 mL of anhydrous THF. The mixture was stirred for 10 minutes or until the solid was completely dissolved. The mixture was cooled to $^-$78° C. using a dry ice and acetone bath. To the mixture was added 19.84 mL of a 2M lithium diisopropylamide solution (0.03967 mol., 1.05 eq.). The addition was done slowly to maintain a temperature below $^-$60° C. After the addition was complete the mixture was allowed to stir for 2.0 hours at $^-$78° C. upon which time the suspension was slowly quenched with 4.70 mL of iodomethane (0.07556 mol., 2.0 eq.). The temperature was not allowed to increase above $^-$50° C. during the addition. The reaction was allowed to slowly warm to room temperature and stir over 16 hours. The solution was filtered away from preciptates and the supernatant reduced to a residue "in vacuo". The residue was taken up in 60 mL of ethyl acetate and was with satd. Sodium bicarbonate solution (50 mL) and satd. NaCl solution (50 mL). The ethyl acetate layer was then dried with 4.5 grams of anhydrous sodium sulfate and filtered. The organic layer was reduced to a residue "in vacuo". The final product was golden oil with a final raw yield of 9.10 grams (62.6% yield). HPLC indicated that that small amounts of the starting material remained along with some dimethylated by-product. This intermediate product was not characterized and was used "as is" in the next step.

The product was a clear liquid that distilled under vacuum at 140° C. at 1 mm Hg. Final yield was 55.38% after distillation.

Quantitative $^{13}$C-NMR (d-CDCl$_2$): $\underline{C}$=O (1C, 176.508 ppm); $\underline{C}_{Ar}$—O (2C, 153.411 & 152.935 ppm); $\underline{C}_{Ar}$—H (4C, 115.09 & 114.299 ppm); $\underline{CH_2}$—CH$_2$—O (1C, 68.186 ppm); CH$_2$—$\underline{CH_2}$—O (1C, 59.782); $\underline{CH}$3O (1C, 55.339 ppm); CH—$\underline{CH_3}$ (1C, 39.239 ppm); —$\underline{CH_2}$— (5C, 33.465, 29.030, 26.888, 25.666 ppm.); CH—$\underline{CH3}$ (1C, 16.835); CH$_2$—$\underline{CH_2}$ (1C, 14.012 ppm).

The resulting product was hydrolyzed according to methods described for compound 47 to produce the compound 80. Yield was 82.3%. Product was an off-white solid. M.P. was 71°-73° C. Elemental Analysis: Theoretical C=68.55%, H=8.63%. Found C=68.04%, H=8.65%; Quantitative $^{13}$C-NMR (d$_6$-DMSO): $\underline{C}$=O (1C, 177.668); $\underline{C}_{Ar}$—O (2C, 153.243 & 152.773 ppm); $\underline{C}_{Ar}$—H (4C, 115.265 & 114.554 ppm); $\underline{CH_2}$—CH$_2$—O (1C, 67.818 ppm); O$\underline{CH_3}$ (1C, 55.305 ppm); CH—$\underline{CH_3}$ (1C, 33.340 ppm); —$\underline{CH_2}$— (5C, 33.340, 28.805, 26.742, 25.487 ppm.); CH—$\underline{CH3}$ (1C, 17.075 ppm)

Preparation of Compound 69

8-(4-methoxy-phenoxy)-2-methyl octanoic acid, ethyl ester was prepared as described above. The resulting product was hydrolyzed according to methods described for compound 47 to produce the compound 69.

Yield was 74.6%. Product was a white solid. M.P. was 96°-97° C. Elemental Analysis: Theoretical C=67.65%, H=8.33%. Found C=67.74%, H=8.44%; Quantitative $^{13}$C-NMR (d$_6$-DMSO): $\underline{C}$=O (1C, 174.628); $\underline{C}_{Ar}$—O (2C, 153.291 & 152.798 ppm); $\underline{C}_{Ar}$—H (4C, 115.251 & 114.562 ppm); $\underline{CH_2}$—CH$_2$—O (1C, 67.844 ppm); O$\underline{CH_3}$ (1C, 55.301 ppm);

$\underline{CH_2}$—C=O (1C, 39.343 ppm); —$\underline{CH_2}$— (5C, 33.747, 28.700, 25.545, 24.575 ppm.)

Preparation of Compound 88

A mixture of 6.525 g (40 mmol) of carsalam, 10.26 g (44 mmol) of 9-bromo-1-nonanol, and 5.30 g (50 mmol) of sodium carbonate in 30 mL N,N-dimethylacetamide (DMA) was heated at 75-80° C. for 3 hours. TLC (eluent: ethyl acetate/heptane) indicated the reaction was completed. The reaction was carefully poured into a mixture of ice-water. The resulting white solid was stirred for 1 hour. It was collected on sintered glass funnel, washed with water, hexane and dried in vacuo to yield 9.80 g of 3-(9-hydroxynonyl)-2H-1,3-benzoxazine-2,4(3H)-dione (80%). To a slurry of 6.11 g (20 mmol) of 3-(9-hydroxynonyl)-2H-1,3-benzoxazine-2,4(3H)-dione in 10 mL of N,N-dimethylacetamide at room temperature was added 20.4 mL (20.4 mmol) of potassium t-butoxide in THF solution. The clear brown solution became very thick. More DMA (10 mL) was added, and the mixture was heated at reflux for 5 minutes. 0.664 g (4 mmol) of potassium iodide was added, followed by dropwise addition of 3.34 (20 mmol) of ethyl bromoacetate. The reaction was refluxed for 1 hour, cooled to about 35° C. and poured into ice-water. A gum resulted. The supernatant liquid was decanted and fresh water was added. That procedure was repeated twice. The gum was dissolved in THF. The THF solution was carefully poured into hexane. The resulting solid was collected, washed with hexane and dried in vacuo. The weight of the desired product was 2.36 g (35%). HPLC: 4.39 min.; Mp: 125-128° C. $^H$NMR (M DSO d$_6$): δ 1.25 (12H, m), 1.37 (2H, m), 1.53 (2H, m), 3.28 (2H, m), 3.36 (2H, t), 4.85 (2H, s), 7.07 (2H, m), 7.45 (1H, t), 7.88 (1H, d), 8.70 (1H, t). Anal. Calcd for $C_{18}H_{27}NO_6$: C, 64.07; H, 8.07; N, 4.15. Found: C, 63.71; H, 8.29; N, 4.31.

Preparation of Compound 93

Melting point: 57-59° C. Combustion analysis: % C, 72.69 (calc'd), 72.75 (found); % H, 9.15 (calc'd), 9.44 (found).

Preparation of Compound 94

Melting point: 59-61° C. Combustion analysis: % C, 71.16 (calc'd), 71.08 (found); % H, 8.53 (calc'd), 8.99 (found).

Preparation of Compound 95

This compound is available from Contact Service Company of Moscow, Russia.

Preparation of Compound 96

This compound is available from Contact Service Company of Moscow, Russia.

Preparation of Compound 97

This compound is available from Sigma Company of Milwaukee, Wis.

Example 2

Salmon Calcitonin (sCT)—Oral Delivery

Oral dosing (PO) compositions of a delivery agent compound and salmon calcitonin (sCT) in deionized water were prepared as described in Table 2 below. Typically, 450 mg of the delivery agent compound was added to 2.0 ml of water. Either the sodium salt of the compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (about 6.5 to 8.5) with NaOH or HCl. 90 μg sCT from a sCT stock solution (2 mg/ml made by adding 1000% pH 4 phosphate buffer to sCT and allowing it to go into solution by sitting for about 10-20 minutes and periodically gently inverting) was added to the solution. Water was then added to bring the total volume to 3.0 ml (varies depending on solubility of the delivery agent compound). The dosing solutions containing delivery agent compounds 3 and 15 required further dilution with water, and final doses of 3 and 2 ml/kg, respectively, were administered to achieve the desired amount of delivery agent compound and sCT. The dosing solutions had a final delivery agent compound dose, sCT dose and dose volume amounts as listed below in Table 2.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=0, 10, 20, 30, 60 and 90 minutes. Serum sCT was determined by testing with an EIA kit (Kit # EIAS-6003 from Peninsula Laboratories, Inc., San Carlos, Calif.). Numbers were adjusted according to baseline values obtained at time=0. The results from the animals in each dosing group were averaged for each time point. The maximum is reported below in Table 2.

TABLE 2

Salmon Calcitonin (sCT) - Oral Delivery

| Delivery Agent Compound | Compound Dose (mg/kg) | sCT Dose (μg/kg) | Dose Volume (ml) | Mean Peak Serum sCT (pg/ml ± SD) (SE) |
|---|---|---|---|---|
| 1 | 150 | 30 | 1 | 317 ± 405 |
| 1 | 150 | 30 | 1 | 398 ± 237 |
| 1 | 150 | 30 | 1 | 410 ± 471 |
| 2 | 150 | 30 | 1 | 628 ± 221 |
| 2 | 150 | 30 | 1 | 449 ± 550 |
| 2 | 150 | 30 | 1 | 320 ± 348 |
| 3 | 150 | 30 | 3 | 0 ± 81 |
| 4 | 150 | 30 | 1 | 187 ± 177 |
| 4 | 150 | 30 | 1 | 195 ± 436 |
| 5 | 150 | 30 | 1 | 349 ± 348 |
| 6 | 150 | 30 | 1 | 316 ± 189 |
| 6 | 150 | 30 | 1 | 144 ± 200 |
| 7 | 150 | 30 | 1 | 677 ± 429 |
| 7 | 150 | 30 | 1 | 87 ± 135 |
| 7 | 150 | 30 | 1 | 149 ± 103 |
| 7 | 150 | 30 | 1 | 216 ± 180 |
| 7 | 150 | 30 | 1 | 313 ± 381 |
| 7 | 150 | 30 | 1.16 | 297 ± 270 |
| 7 | 150 | 30 | 1 | 181 ± 197 |
| 7 | 50 | 100 | 0.5 | 81 ± 137 |
| 7 | 50 | 100 | 0.5 | 273 ± 303 |
| 7 | 50 | 100 | 1 | 116 ± 170 |
| 7 | 150 | 30 | 1 | 148 ± 152 |
| 7 | 150 | 30 | 1 | 0 |
| 7 | 150 | 30 | 1 | 279 ± 369 |
| 7 | 150 | 30 | 1 | 220 ± 126 |
| 7 | 150 | 30 | 1 | 438 ± 154 |
| 7 | 150 | 30 | 1 | 86 ± 146 |
| 8 | 150 | 30 | 1 | 166 ± 190 |
| 8 | 150 | 30 | 1 | 194 ± 239 |
| 8 | 150 | 30 | 2 | 36 ± 49 |
| 8 | 150 | 30 | 1 | 327 ± 323 |
| 9 | 150 | 30 | 1 | 278 ± 286 |
| 9 | 150 | 30 | 1 | 133 ± 172 |
| 9 | 150 | 30 | 1 | 255 ± 249 |
| 9 | 150 | 30 | 1 | 286 ± 126 |
| 10 | 150 | 30 | 1 | 246 ± 212 |
| 10 | 150 | 30 | 1 | 119 ± 131 |
| 10 | 150 | 30 | 1 | 100 ± 224 |
| 10 | 150 | 30 | 1 | 352 ± 445 |
| 11 | 150 | 30 | 1 | 526 ± 415 |
| 12 | 150 | 30 | 1 | 391 ± 278 |
| 12 | 50 | 100 | 1 | 316 ± 476 |
| 12 | 50 | 100 | 0.5 | 445 ± 221 |
| 12 | 150 | 30 | 1 | 224 ± 106 |
| 12 | 150 | 30 | 1 | 170 ± 233 |
| 12 | 150 | 30 | 1 | 286 ± 267 |
| 12 | 150 | 30 | 1 | 195 ± 172 |
| 12 | 150 | 30 | 1 | 150 ± 132 |
| 12 | 150 | 30 | 1 | 273 ± 206 |
| 12 | 150 | 30 | 1 | 170 ± 48 |
| 12 | 150 | 30 | 1 | 0 ± 98 |
| 12 | 150 | 30 | 1 | 151 ± 80 |
| 12 | 150 | 30 | 1 | 314 ± 255 |
| 12 | 150 | 30 | 1 | 184 ± 177 |

TABLE 2-continued

Salmon Calcitonin (sCT) - Oral Delivery

| Delivery Agent Compound | Compound Dose (mg/kg) | sCT Dose (µg/kg) | Dose Volume (ml) | Mean Peak Serum sCT (pg/ml ± SD) (SE) |
|---|---|---|---|---|
| 12 | 150 | 30 | 1 | 412 ± 275 |
| 12 | 150 | 30 | 1 | 79 ± 92 |
| 12 | 150 | 30 | 1 | 168 ± 169 |
| 12 | 150 | 30 | 1 | 206 ± 286 |
| 12 | 150 | 30 | 1 | 293 ± 414 |
| 12 | 150 | 30 | 1 | 180 ± 263 |
| 12 | 150 | 30 | 1 | 226 ± 148 |
| 12 | 150 | 30 | 1 | 507 ± 413 |
| 12 | 150 | 30 | 1 | 177 ± 188 |
| 12 | 150 | 30 | 1 | 203 ± 227 |
| 12 | 150 | 30 | 1 | 330 ± 462 |
| 12 | 150 | 30 | 1 | 160 ± 188 |
| 12 | 150 | 30 | 1 | 291 ± 269 |
| 12 | 150 | 30 | 1 | 170 ± 246 |
| 12 | 150 | 30 | 1 | 199 ± 236 |
| 12 | 150 | 30 | 1 | 137 ± 133 |
| 12 | 150 | 30 | 1 | 207 ± 164 |
| 12 | 150 | 30 | 1 | 203 ± 120 |
| 12 | 150 | 30 | 1 | 182 ± 153 |
| 12 | 150 | 30 | 1 | 181 ± 270 |
| 12 | 150 | 30 | 1 | 219 ± 262 |
| 12 | 150 | 30 | 1 | 276 ± 163 |
| 12 | 150 | 30 | 1 | 196 ± 131 |
| 12 | 150 | 30 | 1 | 185 ± 192 |
| 12 | 150 | 30 | 1 | 75 ± 169 |
| 12 | 150 | 30 | 1 | 125 ± 164 |
| 12 | 150 | 30 | 1 | 118 ± 265 |
| 12 | 150 | 30 | 1 | 207 ± 207 |
| 12 | 150 | 30 | 1 | 224 ± 313 |
| 12 | 150 | 30 | 1 | 190 ± 244 |
| 12 | 150 | 30 | 1 | 336 ± 347 |
| 12 | 150 | 30 | 1 | 209 ± 118 |
| 12 | 150 | 30 | 1 | 302 ± 257 |
| 12 | 150 | 30 | 1 | 225 ± 258 |
| 12 | 150 | 30 | 1 | 227 ± 233 |
| 12 | 150 | 30 | 1 | 172 ± 296 |
| 14 | 150 | 30 | 1 | 568 ± 247 |
| 14 | 150 | 30 | 1 | 199 ± 180 |
| 14 | 150 | 30 | 1 | 117 ± 166 |
| 14 | 150 | 30 | 1 | 196 ± 155 |
| 15 | 150 | 30 | 2 | 116 ± 88 |
| 18 | 150 | 30 | 2 | 14 ± 4183 |
| 19 | 150 | 30 | 1 | 206 ± 131 |
| 19 | 150 | 30 | 1 | 79 ± 176 |
| 19 | 150 | 30 | 1 | 224 ± 501 |
| 19 | 150 | 30 | 1 | 110 ± 125 |
| 19 | 150 | 30 | 1 | 170 ± 161 |
| 19 | 150 | 30 | 1 | 128 ± 155 |
| 20 | 150 | 30 | 1 | 138 ± 107 |
| 20 | 150 | 30 | 1 | 85 ± 82 |
| 20 | 150 | 30 | 1 | 96 ± 135 |
| 21 | 150 | 30 | 1 | 181 ± 128 |
| 21 | 150 | 30 | 1 | 215 ± 232 |
| 21 | 150 | 30 | 1 | 89 ± 98 |
| 22 | 150 | 30 | 1 | 309 ± 152 |
| 22 | 150 | 30 | 1 | 290 ± 174 |
| 22 | 150 | 30 | 1 | 273 ± 281 |
| 22 | 150 | 30 | 1 | 148 ± 162 |
| 23 | 150 | 30 | 1 | 161 ± 150 |
| 23 | 150 | 30 | 1 | 122 ± 273 |
| 24 | 150 | 30 | 1 | 142 ± 135 |
| 24 | 150 | 30 | 1 | 21 ± 48 |
| 24 | 150 | 30 | 1 | 665 ± 1487 |
| 25 | 150 | 30 | 1 | 53 ± 77 |
| 27 | 150 | 30 | 1 | 163 ± 106 |
| 28 | 150 | 30 | 1 | 138 ± 90 |
| 29 | 150 | 30 | 1 | 233 ± 207 |
| 29 | 150 | 30 | 1 | 193 ± 215 |
| 29 | 150 | 30 | 1 | 92 ± 408 |
| 30 | 150 | 30 | 1 | 166 ± 185 |
| 30 | 150 | 30 | 1 | 166 ± 106 |
| 30 | 150 | 30 | 1 | 122 ± 119 |
| 30 | 150 | 30 | 1 | 313 ± 487 |
| 31 | 150 | 30 | 1 | 165 ± 119 |
| 31 | 150 | 30 | 1 | 70 ± 99 |
| 31 | 150 | 30 | 1 | 84 ± 78 |
| 32 | 150 | 30 | 1 | 175 ± 148 |
| 32 | 150 | 30 | 1 | 103 ± 75 |
| 32 | 150 | 30 | 1 | 187 ± 135 |
| 33 | 150 | 30 | 1 | 96 ± 209 |
| 34 | 150 | 30 | 1 | 103 ± 72 |
| 34 | 150 | 30 | 1 | 137 ± 178 |
| 36 | 150 | 30 | 1 | 0 ± 62 |
| 37 | 150 | 30 | 1 | 126 ± 48 |
| 37 | 150 | 30 | 1 | 149 ± 184 |
| 37 | 150 | 30 | 1 | 179 ± 232 |
| 37 | 150 | 30 | 1 | 63 ± 91 |
| 38 | 150 | 30 | 1 | 200 ± 158 |
| 38 | 150 | 30 | 1 | 104 ± 130 |
| 39 | 150 | 30 | 1 | 115 ± 120 |
| 39 | 150 | 30 | 1 | 115 ± 178 |
| 43 | 150 | 30 | 1 | 50 ± 71 |
| 44 | 150 | 30 | 1 | 188 ± 184 |
| 45 | 150 | 30 | 1 | 125 ± 187 |
| 45 | 150 | 30 | 1 | 172 ± 158 |
| 47 | 150 | 30 | 1 | 62 ± 99 |
| 48 | 150 | 30 | 4 | 35 ± 49 |
| 48 | 150 | 30 | 3 | 95 ± 156 |
| 49 | 150 | 30 | 1 | 479 ± 291 |
| 49 | 150 | 30 | 1 | 170 ± 75 |
| 49 | 150 | 30 | 1 | 89 ± 129 |
| 51 | 150 | 30 | 1 | 49 ± 45 |
| 51 | 150 | 30 | 1 | 203 ± 227 |
| 51 | 150 | 30 | 1 | 207 ± 207 |
| 51 | 150 | 30 | 1 | 226 ± 220 |
| 52 | 150 | 30 | 1 | 163 ± 300 |
| 54 | 150 | 30 | 1 | 34 ± 47 |
| 56 | 150 | 30 | 1 | 165 ± 243 |
| 56 | 150 | 30 | 1 | 90 ± 125 |
| 56 | 150 | 30 | 1 | 113 ± 115 |
| 56 | 150 | 30 | 1 | 175 ± 150 |
| 62 | 150 | 30 | 1 | 117 ± 158 |
| 64 | 150 | 30 | 1 | 138 ± 148 |
| 66 | 150 | 30 | 4 | 109 ± 244 |
| 67 | 150 | 30 | 2 | 681 ± 419 |
| 67 | 150 | 30 | 1 | 142 ± 142 |
| 67 | 150 | 30 | 1 | 256 ± 158 |
| 71 | 150 | 30 | 2 | 302 ± 246 |
| 71 | 150 | 30 | 1 | 45 ± 62 |
| 71 | 150 | 30 | 1 | 146 ± 328 |
| 72 | 150 | 30 | 1 | 558 ± 576 |
| 72 | 150 | 30 | 1 | 224 ± 409 |
| 78 | 150 | 30 | 1 | 54 ± 121 |
| 78 | 150 | 30 | 1 | 154 ± 167 |
| 78 | 150 | 30 | 1 | 107 ± 158 |
| 79 | 150 | 30 | 1 | 133 ± 90 |

Example 3

Recombinant Human Growth Hormone (rhGH)

Oral Delivery

Oral gavage (PO) dosing solutions of delivery agent compound and rhGH in phosphate buffer were prepared by mixing. A solution of the delivery agent compound was made either with the sodium salt of the delivery agent compound or by converting the free acid to its sodium salt. Typically, a solution of the delivery agent compound was prepared in phosphate buffer and stirred, adding one equivalent of sodium hydroxide (1.0 N) when making the sodium salt. The final dosing solutions were prepared by mixing the delivery agent compound solution with an rhGH stock solution (15 mg rhGH/ml made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The pH was adjusted, if necessary, to between about 7 and 8.5. The delivery agent compounds and rhGH dose amounts are listed below in Table 3.

The typical dosing and sampling protocols were as follows. Male Sprague-Dawley rats weighing 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery typically at time=15, 30, 45, 60 and 90 minutes. The five samples from each time period were pooled (except for those samples for which standard deviation (SD) and standard error (SE) are reported). Serum rHGH concentrations were quantified by an rHGH immunoassay test kit (Kit # K1F4015 from Genzyme Corporation Inc., Cambridge, Mass.). Previous studies indicated baseline values of about zero. The maximum concentration for each group is reported below in Table 3.

TABLE 3 rhGH - Oral Delivery

| Delivery Agent Compound | Delivery Agent Compound Dose (mg/kg) | rhGH Dose (mg/kg) | Volume dose (ml) | Mean Peak Serum [rhGH] (ng/ml) |
|---|---|---|---|---|
| 1 | 200 | 3 | 1 | 95.5 |
| 1 | 200 | 3 | 1 | 30.9 |
| 1 | 200 | 3 | 1 | 76.2 |
| 1 | 200 | 3 | 1 | 37.2 ± 50 |
| 4 | 200 | 3 | 1 | 12.6 |
| 5 | 200 | 3 | 1 | 127 |
| 5 | 200 | 3 | 1 | 223 |
| 5 | 200 | 3 | 1 | 56.5 |
| 7 | 200 | 3 | 1 | 8.8 |
| 7 | 200 | 3 | 1 | 58.9 |
| 7 | 200 | 3 | 1 | 29.1 ± 58.2 |
| 8 | 200 | 3 | 1 | 4.88 |
| 9 | 200 | 3 | 1 | 1 |
| 10 | 200 | 3 | 1 | 34.3 |
| 11 | 200 | 3 | 1 | 35.4 |
| 12 | 200 | 3 | 1 | 12.7 |
| 12 | 200 | 3 | 1 | 44.3 |
| 14 | 200 | 3 | 1 | 19.8 |
| 15 | 200 | 3 | 1 | 83.9 |
| 15 | 200 | 3 | 1 | 47.3 |
| 15 | 200 | 3 | 1 | 44.7 |
| 15 | 200 | 3 | 1 | 27.4 ± 37.3 |
| 18 | 200 | 3 | 1 | 223 |
| 18 | 162 | 2.6 | 1 | 3.1 |
| 19 | 200 | 3 | 1 | 39.5 |
| 20 | 200 | 3 | 1 | 22.6 |
| 21 | 200 | 3 | 1 | 19.6 |
| 22 | 200 | 3 | 1 | 0 |
| 24 | 200 | 3 | 1 | 1.76 |
| 25 | 200 | 3 | 1 | 0 |
| 26 | 200 | 3 | 1 | 8.3 |
| 27 | 200 | 3 | 1 | 12.9 |
| 28 | 200 | 3 | 1 | 90.1 |
| 28 | 200 | 3 | 1 | 121 |
| 28 | 200 | 3 | 1 | 19.2 |
| 29 | 200 | 3 | 1 | 0 |
| 30 | 200 | 3 | 1 | 40.5 |
| 30 | 200 | 3 | 1 | 0 |
| 30 | 200 | 3 | 1 | 0 |
| 30 | 200 | 3 | 1 | 5.27 |
| 32 | 200 | 3 | 1 | 0 |
| 33 | 200 | 3 | 1 | 10.1 |
| 33 | 200 | 3 | 1 | 6.9 |
| 34 | 200 | 3 | 1 | 0 |
| 34 | 200 | 3 | 1 | 7.8 |
| 36 | 200 | 3 | 1 | 0 |
| 37 | 200 | 3 | 1 | 29 |
| 39 | 200 | 3 | 1 | 0 |
| 43 | 200 | 3 | 1 | 9.49 |
| 43 | 200 | 3 | 1 | 42.2 ± 41 |
| 45 | 200 | 3 | 1 | 11.2 |
| 45 | 200 | 3 | 1 | 22.8 |
| 45 | 200 | 3 | 1 | 42.9 |
| 47 | 200 | 3 | 1 | 11.6 |
| 47 | 200 | 3 | 1 | 144 |
| 47 | 200 | 3 | 1 | 81.7 |
| 47 | 200 | 3 | 1 | 41.7 |
| 47 | 200 | 3 | 1 | 85.7 |
| 47 | 200 | 3 | 2 | 9.9 ± 22.1 |
| 47 | 200 | 3 | 1 | 34.1 ± 42.2 |
| 47 | 200 | 3 | 1 | 9.41 |
| 47 | 200 | 3 | 1 | 132 |
| 49 | 200 | 3 | 1 | 41.3 |
| 49 | 200 | 3 | 1 | 0 |
| 49 | 200 | 3 | 1 | 20.1 |
| 52 | 200 | 3 | 1 | 0 |
| 54 | 200 | 3 | 1 | 6.37 |
| 55 | 200 | 3 | 1 | 12.4 |
| 56 | 200 | 3 | 1 | 0 |
| 60 | 200 | 3 | 1 | 1.5 ± 3.3 |
| 62 | 200 | 3 | 1 | 6.2 |
| 64 | 200 | 3 | 1 | 5 |
| 66 | 200 | 3 | 1 | 0 |
| 67 | 200 | 3 | 1 | 15 |
| 67 | 200 | 3 | 1 | 14.7 |
| 71 | 200 | 3 | 3 | 5.94 |
| 72 | 200 | 3 | 1 | 28 |
| 78 | 200 | 3 | 1 | 0 |
| 79 | 200 | 3 | 1 | 1.48 |
| 79 | 200 | 3 | 1 | 17.8 |

Example 4

Heparin—Oral/Intracolonic Delivery

Oral gavage (PO) and/or intracolonic (IC) dosing solutions containing a delivery agent compound and heparin sodium USP were prepared in 25% aqueous propylene glycol. Either the sodium salt of the delivery agent compound was used or the free acid was converted to the sodium salt with one equivalent of sodium hydroxide. Typically, the delivery agent compound and heparin (about 166-182 IU/mg (typically 166.9 IU/mg)) were mixed by vortex as dry powders. This dry mixture was dissolved in 25% v/v aqueous propylene glycol, vortexed, and placed in a sonicator (about 37° C.). The pH was adjusted to about 7 (6.5 to 8.5) with aqueous NaOH (2N). The dosing solution was sonicated to produce a clear solution. The final volume was adjusted to about 3.0 ml. The final delivery agent compound dose, heparin dose, and dose volume amounts are listed below in Table 4.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing and again as needed to maintain anesthesia. A dosing group of five animals was administered one of the dosing solutions. For oral gavage (PO) dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger. For intracolonic (IC) dosing, a 7.5 cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.25, 0.5, 1.0 and 1.5 hours after dosing. Heparin absorption was verified by an increase in clotting time measured by the activated partial thromboplastin time (APTT) according to the method of Henry, J. B., Clinical Diagnosis and Management by Laboratory Methods, Philadelphia, Pa., W. R. Saunders (1979). Previous studies indicated baseline values of about 20 seconds. Results from the animals in each group were averaged for each time point and the highest of these averages (i.e., mean peak APTT) is reported below in Table 4.

TABLE 4

Heparin - Oral/Intracolonic Delivery

| Delivery Agent Compound | Method of Administration | Delivery Agent Compound Dose (mg/kg) | Heparin Dose (mg/kg) | Volume Dose (ml) | Mean Peak APTT (sec) ± SD |
|---|---|---|---|---|---|
| 1 | IC | 50 | 25 | 1 | 130.84 ± 118.18 |
| 1 | IC | 50 | 25 | 1 | 231.34 |
| 2 | IC | 50 | 25 | 1 | 48.788 ± 32.79 |
| 3 | IC | 50 | 25 | 1 | 16.046 ± 0.481 |
| 3 | IC | 50 | 25 | 1 | 16.984 ± 1.45 |
| 4 | IC | 50 | 25 | 1 | 40.3 ± 17.8 |
| 4 | IC | 50 | 25 | 1 | 23.076 ± 4.72 |
| 4 | IC | 50 | 25 | 1 | 37.148 ± 39.67 |
| 5 | PO | 300 | 100 | 3 | 135.7 ± 17.3 |
| 6 | IC | 50 | 25 | 1 | 157.4 ± 33.7 |
| 6 | PO | 300 | 100 | 3 | 193 ± 61.2 |
| 6 | IC | 50 | 25 | 1 | 99.8 ± 50.6 |
| 7 | IC | 50 | 25 | 1 | 130.5 ± 42.6 |
| 7 | IC | 50 | 25 | 1 | 92 ± 40.3 |
| 7 | IC | 50 | 25 | 1 | 99.4 ± 25.5 |
| 8 | IC | 50 | 25 | 1 | 251.94 ± 67.96 |
| 9 | IC | 50 | 25 | 1 | 21.45 ± 1.71 |
| 10 | IC | 50 | 25 | 1 | 81.8 ± 7 |
| 10 | IC | 50 | 25 | 1 | 63.5 |
| 11 | IC | 50 | 25 | 1 | 39.53 ± 8.25 |
| 12 | IC | 50 | 25 | 1 | 219.5 ± 128.4 |
| 12 | IC | 50 | 25 | 1 | 169.6 ± 68.6 |
| 12 | PO | 300 | 100 | 3 | 201.4 ± 45.7 |
| 12 | IC | 50 | 25 | 1 | 115.81 ± 159.53 |
| 12 | IC | 50 | 25 | 1 | 236.8 |
| 12 | IC | 50 | 25 | 1 | 300 |
| 12 | IC | 50 | 25 | 1 | 255.452 ± 41.99 |
| 12 | IC | 50 | 25 | 1 | 167.08 ± 81.62 |
| 12 | IC | 50 | 25 | 1 | 195.884 ± 142.628 |
| 12 | IC | 50 | 25 | 1 | 279.076 ± 46.79 |
| 12 | IC | 50 | 25 | 1 | 220.164 ± 109.57 |
| 12 | IC | 50 | 25 | 1 | 300 |
| 22 | IC | 50 | 25 | 1 | 287.9 ± 120.1 |
| 26 | IC | 50 | 25 | 1 | 76.7 |
| 26 | IC | 50 | 25 | 1 | 41.534 ± 25.56 |
| 27 | IC | 50 | 25 | 1 | 85.7 |
| 27 | IC | 50 | 25 | 1 | 279.182 ± 46.55 |
| 28 | IC | 50 | 25 | 1 | 143.6 ± 44 |
| 28 | IC | 50 | 25 | 1 | 251.1 ± 109.34 |
| 29 | IC | 50 | 25 | 1 | 105.01 ± 115.28 |
| 29 | IC | 50 | 25 | 1 | 111.46 ± 108.58 |
| 30 | IC | 50 | 25 | 1 | 50.9 ± 20.5 |
| 31 | IC | 50 | 25 | 1 | 47 ± 23.1 |
| 32 | IC | 50 | 25 | 1 | 26.5 ± 2.3 |
| 35 | IC | 50 | 25 | 1 | 65.8 ± 35.5 |
| 47 | IC | 50 | 25 | 1 | 370.3 ± 97.8 |
| 51 | IC | 50 | 25 | 1 | 92.5 ± 41.5 |
| 54 | IC | 50 | 25 | 1 | 31.56 ± 7.54 |
| 62 | IC | 50 | 25 | 1 | 152.41 ± 136.63 |
| 62 | IC | 50 | 25 | 1 | 91.204 ± 117.43 |
| 64 | IC | 50 | 25 | 1 | 220.988 ± 122.2 |
| 64 | IC | 50 | 25 | 1 | 125.372 ± 114.72 |

Example 5

Low Molecular Weight Heparin (LMWH)—Oral/Intracolonic Delivery

Oral dosing (PO) and/or intracolonic (IC) compositions containing a delivery agent compound and low molecular weight heparin (LMWH) were prepared in 25% aqueous propylene glycol. Either the sodium salt of the delivery agent compound was used or the free acid was converted to the sodium salt with one equivalent of sodium hydroxide. Typically, the delivery agent compound and LMWH (Parnaparin, 91 IU/mg average molecular weight about 5,000, available from Opocrin, Modena, Italy)(typically 90-105 IU/mg, average molecular weight about 5,000) were mixed by vortex as dry powders. This dry mixture was dissolved in 25% v/v aqueous propylene glycol, vortexed, and placed in a sonicator (37° C.) to produce a clear solution. The pH was adjusted to about 7 (6.5-8.5) with 2N aqueous NaOH. The dosing solution was sonicated to produce a clear solution. The final volume was adjusted to 3.0 ml. The final delivery agent compound dose, LMWH dose, and dose volume amounts are listed below in Table 5.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing and again as needed to maintain anesthesia. A dosing group of five animals was administered one of the dosing solutions. For oral gavage (PO) dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger. For intracolonic (IC) dosing, a 7.5 cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.5, 1.0, 2.0, 3.0 and 4.0 hours after dosing. LMWH absorption was verified by an increase in plasma LMWH measured by the anti-Factor Xa assay CHROMOSTRATE™ Heparin anti-$X_a$ assay (available from Organon Teknika Corporation, Durham, N.C.). Plasma LMWH concentrations from the animals in each group were averaged for each time point and these mean plasma LMWH concentrations were plotted against time. The peak of these mean plasma LMWH concentrations is reported below in Table 5.

TABLE 5

LMWH - Oral/Intracolonic Delivery

| Delivery Agent Compound | Method of Administration | Delivery Agent Compound Dose (mg/kg) | LMWH Dose (IU/kg) | Volume Dose (ml/kg) | Mean Peak Plasma LMWH Concentration (IU/ml) ± SD |
|---|---|---|---|---|---|
| 1 | IC | 50 | 750 | 1 | 1.038 ± 0.338 |
| 1 | IC | 50 | 750 | 1 | 1.734 ± 0.192 |
| 1 | IC | 25 | 750 | 1 | 1.022 ± 0.432 |
| 2 | IC | 50 | 750 | 1 | 1.038 ± 0.338 |
| 6 | IC | 25 | 750 | 1 | 0.47 ± 0.17 |
| 7 | PO | 300 | 3000 | 3 | 0.5 ± 0.412 |
| 7 | IC | 50 | 750 | 1 | 1.264 ± 0.207 |
| 7 | IC | 50 | 750 | 1 | 1.716 ± 0.105 |
| 7 | IC | 25 | 750 | 1 | 0.9 ± 0.252 |
| 9 | IC | 50 | 750 | 1 | 0.474 ± 0.095 |
| 10 | IC | 50 | 750 | 1 | 0.088 ± 0.121 |
| 11 | IC | 50 | 750 | 1 | 0.91 ± 0.414 |
| 12 | PO | 300 | 3000 | 3 | 0.137 ± 0.18 |
| 12 | IC | 50 | 751 | 1 | 1.5 ± 0.23 |
| 12 | IC | 50 | 750 | 1 | 1.7 ± 0.308 |
| 12 | IC | 50 | 750 | 1 | 1.74 ± 0.304 |
| 12 | IC | 50 | 750 | 1 | 2.012 ± 0.124 |
| 12 | IC | 25 | 750 | 1 | 1.66 ± 0.302 |
| 12 | IC | 25 | 750 | 1 | 0.974 ± 0.503 |
| 12 | IC | 10 | 750 | 1 | 0.2 ± 0.077 |
| 12 | IC | 25 | 750 | 1 | 0.624 ± 0.247 |
| 12 | IC | 50 | 750 | 1 | 1.498 ± 0.462 |
| 19 | IC | 50 | 750 | 1 | 0.65 ± 0.37 |
| 22 | IC | 50 | 750 | 1 | 1.842 ± 0.205 |
| 22 | IC | 25 | 750 | 1 | 1.496 ± 0.153 |
| 22 | IC | 10 | 750 | 1 | 0.396 ± 0.153 |
| 26 | IC | 50 | 750 | 1 | 0.262 ± 0.106 |
| 27 | IC | 50 | 750 | 1 | 1.622 ± 0.265 |
| 28 | IC | 50 | 750 | 1 | 1.64 ± 0.45 |
| 28 | IC | 25 | 750 | 1 | 1.43 ± 0.31 |
| 30 | IC | 50 | 750 | 1 | 0.162 ± 0.094 |
| 30 | IC | 50 | 750 | 1 | 0.288 ± 0.152 |
| 31 | IC | 50 | 750 | 1 | 0.47 ± 0.287 |
| 31 | IC | 50 | 750 | 1 | 0.47 ± 0.332 |
| 32 | IC | 50 | 750 | 1 | 0.07 ± 0.01 |
| 54 | IC | 50 | 750 | 1 | 3.046 ± 0.422 |
| 65 | IC | 50 | 750 | 1 | 0.642 |
| 66 | IC | 50 | 750 | 1 | 0.952 |
| 66 | IC | 50 | 750 | 1 | 1.114 ± 0.254 |

Example 6

Parathyroid Hormone (PTH 1-34)

Oral/Intracolonic Delivery

Oral gavage (PO) and/or intracolonic (IC) dosing solutions of delivery agent compound and human parathyroid hormone residues 1-34 (PTH) in deionized water were prepared. A solution of the compound was made either with the sodium salt of the delivery agent compound or by converting the free acid to its sodium salt. Typically, a solution of the delivery agent compound was prepared in water and stirred, adding one equivalent of sodium hydroxide (1.0 N) when making the sodium salt. The final dosing solutions were prepared by mixing the compound solution with a PTH stock solution (typically in water having a concentration of 5 mg PTH/ml) and diluting to the desired volume (usually 3.0 ml). The pH was adjusted, if necessary, to between about 7 and 8.5. The final compound and PTH doses, and the dose volumes are listed below in Table 6.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The dosing solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 minutes for IC dosing. Serum PTH concentrations were quantified by a PTH radioimmunoassay kit (Kit # RIK 6101 from Peninsula Laboratories, Inc., San Carlos, Calif.). Previous studies indicated baseline values of about zero. Results from the animals in each group were averaged for each time point. The maximum of these averages (i.e., the mean peak serum PTH concentration) is reported below in Table 6.

TABLE 6

PTH Oral (PO) Delivery

| Delivery Compound # | Delivery Agent Compound Dose (mg/kg) | PTH Dose (μg/kg) | Volume dose (ml/kg) | Mean Peak Serum [PTH] (pg/mL) ± SD |
|---|---|---|---|---|
| 12 | 100 | 200 | 1 | 276 ± 252 |
| 30 | 100 | 200 | 1 | 78 ± 71 |
| 31 | 100 | 200 | 1 | 460 ± 194 |
| 33 | 100 | 200 | 1 | 837 ± 347 |
| 34 | 100 | 200 | 1 | 538 ± 328 |
| 51 | 100 | 200 | 1 | 420 ± 305 |
| 51 | 100 | 200 | 1 | 287 ± 120 |
| 51 | 100 | 200 | 1 | 478 ± 230 |
| 51 | 100 | 200 | 1 | 798 ± 518 |

Example 7

Interferon—Oral Delivery

Dosing solutions of delivery agent compound and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted to about 7.0 to 8.5. The delivery agent compound solution was mixed with an IFN stock solution (about 22.0 to 27.5 mg/ml in phosphate buffered saline) and diluting to the desired volume (usually 3.0 ml). The final delivery agent compound and IFN doses, and the dose volumes are listed below in Table 7.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 45, 60 and 90 minutes. Serum IFN concentrations were quantified using Cytoscreen Immunoassay Kit for human IFN-alpha (catalog # KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 7,

TABLE 7

Interferon - Oral Delivery

| Delivery Agent Compound | Delivery Agent Compound Dose (mg/kg) | IFN Dose (mg/kg) | Volume dose (ml/kg) | Mean Peak Serum [IFN] (ng/ml) ± SD |
|---|---|---|---|---|
| 1 | 200 | 1 | 1 | 17.357 ± 38 |
| 5 | 200 | 1 | 1 | 5.1042 ± 3.4 |
| 5 | 50 | 0.5 | 1 | 1.54 ± 0.26 |
| 5 | 200 | 1 | 1 | 1.1838 ± 1.42 |
| 5 | 50 | 0.5 | 1 | 2.1 ± 0.95 |
| 5 | 200 | 1 | 1 | 1.51 ± 1.9 |
| 5 | 200 | 1 | 1 | 4.11 ± 2 |
| 5 | 200 | 1 | 1 | 7.5769 ± 5 |
| 6 | 200 | 1 | 1 | 0.5696 ± 0.8 |
| 7 | 400 | 1 | 1 | 0.223 |
| 7 | 200 | 1 | 1 | 3.9308 ± 3.2 |
| 12 | 200 | 1 | 1 | 1.6362 ± 1.68 |
| 15 | 200 | 1 | 1 | 6.0324 ± 2.8 |
| 28 | 200 | 1 | 1 | 2.185 ± 2.68 |
| 28 | 200 | 1 | 1 | 0.8 ± 1.7 |
| 32 | 200 | 1 | 1 | 0 |
| 43 | 200 | 1 | 1 | 1 ± 2.1 |
| 43 | 200 | 1 | 1 | 1.206 |
| 47 | 200 | 1 | 1 | 1.1 ± 0.85 |
| 59 | 200 | 1 | 1 | 0.56 ± 1 |
| 59 | 200 | 1 | 1 | 0 |
| 67 | 200 | 1 | 1 | 3.4451 ± 4.5 |
| 73 | 200 | 1 | 1 | 0.76 ± 0.7 |
| 73 | 200 | 1 | 1 | 0.22 ± 0.5 |

Example 8

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed below in Table 8.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations ($\mu$U/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 8.

TABLE 8

Insulin - Oral Delivery

| Delivery Agent Compound | Delivery Agent Compound Dose (mg/kg) | Insulin Dose (mg/kg) | Volume dose (ml/kg) | Mean Peak Serum [INS] ± SD |
|---|---|---|---|---|
| 1 | 100 | 3 | 1 | 74.237 ± 1144.49 |
| 3 | 200 | 0.5 | 1 | 29.95 ± 46.13 |
| 6 | 200 | 0.5 | 1 | 129.5 ± 131.5 |
| 7 | 100 | 3 | 1 | 130.9724 ± 83.7 |

TABLE 8-continued

Insulin - Oral Delivery

| Delivery Agent Compound | Delivery Agent Compound Dose (mg/kg) | Insulin Dose (mg/kg) | Volume dose (ml/kg) | Mean Peak Serum [INS] ± SD |
|---|---|---|---|---|
| 7 | 200 | 0.5 | 1 | 88.06 ± 33.72 |
| 7 | 200 | 0.5 | 1 | 320.1 ± 520.4 |
| 7 | 200 | 0.5 | 1 | 200.2 ± 118.7 |
| 7 | 200 | 0.5 | 1 | 164.2 ± 134.7 |
| 7 | 200 | 0.5 | 1 | 214.7 ± 100.86 |
| 7 | 200 | 0.5 | 1 | 56.71 ± 47.04 |
| 7 | 200 | 0.5 | 1 | 17.4 ± 21.8 |
| 8 | 200 | 0.5 | 1 | 13.14 ± 6.81 |
| 10 | 100 | 3 | 1 | 63.5884 ± 129.23 |
| 12 | 100 | 3 | 0.5 | 205.4 ± 333.4 |
| 15 | 100 | 3 | 1 | 1332.2 ± 1906.4 |
| 15 | 200 | 0.5 | 1 | 540.7 ± 580.12 |
| 15 | 200 | 0.5 | 1 | 18.62 ± 12.54 |
| 15 | 200 | 0.5 | 1 | 155.6 ± 125.2 |
| 15 | 200 | 0.5 | 1 | 169.3 ± 140.78 |
| 19 | 200 | 0.5 | 1 | 4.32 ± 1.39 |
| 20 | 200 | 0.5 | 1 | 27.68 ± 12.5 |
| 21 | 200 | 0.5 | 1 | 14.46 ± 21.61 |
| 22 | 200 | 0.5 | 1 | 24.16 ± 28.11 |
| 25 | 100 | 3 | 1 | 47.2162 ± 31.43 |
| 26 | 100 | 3 | 0.5 | 240.5 ± 528.29 |
| 30 | 200 | 0.5 | 1 | 21.88 ± 13.4 |
| 31 | 100 | 3 | 0.5 | 21.26 ± 6.22 |
| 32 | 200 | 3 | 1 | 6.38 ± 4.42 |
| 32 | 200 | 0.5 | 1 | 3.12 ± 2.26 |
| 33 | 100 | 3 | 0.5 | 58.13 ± 52.86 |
| 33 | 200 | 0.5 | 1 | 110 ± 128 |
| 33 | 200 | 0.5 | 1 | 14.88 ± 11.53 |
| 35 | 200 | 0.5 | 1 | 132.3 ± 154.5 |
| 38 | 100 | 3 | 1 | 74.6542 ± 57.28 |
| 43 | 200 | 0.5 | 1 | 82.81 ± 46.8 |
| 43 | 200 | 0.5 | 1 | 38.68 ± 35.09 |
| 44 | 100 | 3 | 0.5 | 97.49 ± 134.1 |
| 44 | 200 | 0.5 | 1 | 17.41 ± 10.47 |
| 44 | 200 | 0.5 | 1 | 46.76 ± 41.19 |
| 45 | 200 | 0.5 | 1 | 70.32 ± 149.1 |
| 49 | 100 | 3 | 0.5 | 335.7 ± 227.05 |
| 57 | 200 | 3 | 1 | 3322 ± 2721 |
| 59 | 200 | 0.5 | 1 | 315.53 ± 154.56 |
| 61 | 200 | 0.5 | 1 | 58.99 ± 27.15 |
| 63 | 100 | 3 | 1 | 7.843 ± 8.527 |
| 68 | 200 | 3 | 1 | 76.23 ± 76.88 |
| 72 | 200 | 3 | 1 | 4702.5 ± 4700.4 |
| 72 | 200 | 0.5 | 1 | 108.33 ± 55.98 |
| 72 | 200 | 0.5 | 1 | 9.81 ± 13.72 |
| 72 | 200 | 0.5 | 1 | 18.56 ± 19.89 |
| 73 | 100 | 3 | 0.5 | 147.66 ± 176.71 |
| 73 | 200 | 0.5 | 1 | 51.26 ± 9.44 |
| 73 | 200 | 0.5 | 1 | 16.01 ± 12.21 |
| 74 | 100 | 3 | 0.5 | 70.69 ± 127.89 |
| 75 | 200 | 0.5 | 1 | 33.88 ± 38.49 |
| 75 | 200 | 0.5 | 1 | 32.54 ± 19.78 |
| 76 | 200 | 0.5 | 1 | 24.72 ± 25.53 |
| 76 | 200 | 0.5 | 1 | 38.74 ± 74.4 |

Example 9

Insulin—Pulmonary Delivery

Dosing compositions of delivery agent compound and human insulin in water were prepared. Typically, to 1.5 mg of delivery agent compound was added deionized water to bring the volume to 1.0 ml, and the solution was vortexed. Either the sodium salt of the delivery agent compound was used or the free acid was converted to the sodium salt by stirring the resultant solution and adding one equivalent of sodium hydroxide (10 N) and diluting with water. The solution was vortexed, then heated (about 37° C.) and sonicated. The pH was adjusted to between about 7.0 to 8.5 with NaOH or HCl. 75 μl human insulin stock solution (2 mg/ml) was added to the solution. (The stock solution was made as follows. To 0.02 g insulin was added 3 ml pH 3.0 HCl solution in deionized water. The pH of the resulting solution was brought to below 3.0 (about 2.6) with HCl and NaOH until the solution was clear. The pH was then raised to 7.6 using NaOH and HCl. The final volume was brought to 10 ml with pH 7.5 deionized water. Final pH 7.59.) Water was then added to bring the total volume to 2.0 ml, and the solution was inverted gently several times. The final delivery agent compound dose, insulin dose and volume dose amounts are listed below in Table 9.

The typical dosing and sampling protocols were as follows. Male Sprague-Dawley rats weighing between 200-250 g were fasted for 24 hours and administered ketamine (44 mg/kg) and chlorpromazine (3.0 mg/kg) 15 minutes prior to dosing and again as needed to maintain anesthesia (using the same amount of ketamine and 1.5 mg/kg chlorpromazine). Typically, a dosing group of five animals was administered one of the dosing solutions. A control group of five animals was dosed insulin alone. A tracheal instillator for rodents, equipped with light (available from Penn Century, Inc., Pittsburgh, Pa.) was filled with dosing solution and inserted down the throat until the needle went into the trachea (confirmed visually). The dosing solution was administered by pressing the plunger.

Blood samples from each animal were collected serially from the tail artery, typically at 5, 15, 30, 60 and 120 minutes after dosing. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum insulin concentrations (μU/ml) were measured for each time point for each of the five animals in each dosing group. The five values for each time point were averaged and the results plotted as serum insulin concentration versus time. The ratio of the area under the curve (AUC) for the test group versus that of the control group is reported below. The ratio of the maximum serum insulin concentration (Cmax) for the test group versus that of the control group is also reported below.

TABLE 9

Pulmonary Delivery of Insulin

| Delivery Agent Compound | Volume dose (ml/kg) | Delivery Agent Compound Dose (mg/kg) | Insulin Dose (mg/kg) | Cmax | Cmax/Cmax (Control) | Mean Ratio of AUC for insulin + compound versus AUC for insulin alone |
|---|---|---|---|---|---|---|
| 1 | 1 | 3 | 100 | 74.237 | — | — |
| 7 | 0.4 | 0.03 | 0.3 | — | 0.53 | — |
| 7 | 1 | 3 | 100 | 130.9724 | — | — |
| 10 | 1 | 3 | 100 | 63.5884 | — | — |

TABLE 9-continued

Pulmonary Delivery of Insulin

| Delivery Agent Compound | Volume dose (ml/kg) | Delivery Agent Compound Dose (mg/kg) | Insulin Dose (mg/kg) | Cmax | Cmax/Cmax (Control) | Mean Ratio of AUC for insulin + compound versus AUC for insulin alone |
|---|---|---|---|---|---|---|
| 20 | 0.4 | 0.03 | 0.3 | — | 0.92 | — |
| 22 | 0.4 | 0.03 | 0.3 | — | 0.60 | — |
| 22 | 0.4 | 0.03 | 0.3 | — | 0.60 | — |
| 22 | 0.4 | 0.03 | 0.3 | — | 0.70 | — |
| 23 | 0.4 | 0.03 | 0.3 | — | 0.65 | — |
| 25 | 1 | 3 | 100 | 47.2162 | — | — |
| 26 | 0.4 | 0.03 | 0.3 | — | 1.78 | — |
| 26 | 0.4 | 0.03 | 0.3 | — | 3.39 | — |
| 36 | 0.4 | 0.03 | 0.3 | — | 1.40 | — |
| 36 | 0.4 | 0.03 | 0.3 | — | 1.01 | — |
| 37 | 0.4 | 0.03 | 0.3 | — | 1.08 | — |
| 38 | 1 | 3 | 100 | 74.6542 | — | — |
| 39 | 0.4 | 0.03 | 0.3 | — | 0.30 | — |
| 43 | 0.4 | 0.03 | 0.3 | — | 1.02 | 1.44 |
| 44 | 0.4 | 0.03 | 0.3 | — | 0.72 | 0.76 |
| 45 | 0.4 | 0.03 | 0.3 | — | 1.02 | 1.01 |
| 47 | 0.4 | 0.03 | 0.3 | — | 0.57 | 0.63 |
| 48 | 0.4 | 0.03 | 0.3 | 135.56 ± 80.96 | — | 1.30 |
| 49 | 0.4 | 0.03 | 0.3 | — | 0.52 | 0.54 |
| 52 | 0.4 | 0.03 | 0.3 | — | 0.50 | — |
| 54 | 0.4 | 0.03 | 0.3 | — | 0.51 | — |
| 55 | 0.4 | 0.03 | 0.3 | — | 0.99 | — |
| 56 | 0.4 | 0.03 | 0.3 | — | 1.24 | — |
| 63 | 1 | 3 | 100 | 7.843 | — | — |
| 66 | 0.4 | 0.03 | 0.3 | — | 0.84 | — |
| 66 | 0.4 | 0.03 | 0.3 | — | 0.63 | — |
| 67 | 0.4 | 0.03 | 0.3 | — | 1.53 | — |
| 67 | 0.4 | 0.03 | 0.3 | — | 1.51 | — |
| 67 | 0.4 | 0.03 | 0.3 | — | 0.64 | — |
| 67 | 0.4 | 0.03 | 0.3 | — | 0.71 | — |
| 67 | 0.4 | 0.03 | 0.3 | — | 2.20 | — |
| 67 | 0.4 | 0.03 | 0.3 | 66.04 ± 47.42 | — | — |
| 67 | 0.4 | 0.03 | 0.06 | 82.23 ± 47.16 | — | — |
| 67 | 0.4 | 0.03 | 0.15 | 84.40 ± 15.06 | — | — |
| 67 | 0.4 | 0.03 | 0.3 | 92.14 ± 36.17 | — | — |
| 67 | 0.4 | 0.03 | 0.3 | 115.04 ± 68.23 | — | — |
| 67 | 0.4 | 0.03 | 0.15 | 91.20 ± 37.30 | — | — |
| 67 | 0.4 | 0.03 | 0.06 | 70.85 ± 36.24 | — | — |
| 71 | 0.4 | 0.03 | 0.3 | — | 1.08 | — |
| 71 | 0.4 | 0.03 | 0.3 | — | 1.53 | — |
| 71 | 0.4 | 0.03 | 0.3 | 57.82 ± 35.28 | — | — |
| 72 | 0.4 | 0.03 | 0.3 | — | 0.96 | — |
| 78 | 0.4 | 0.03 | 0.3 | — | 1.01 | — |
| 78 | 0.4 | 0.03 | 0.3 | — | 1.46 | — |
| 78 | 0.4 | 0.03 | 0.3 | 80.56 ± 30.51 | — | — |
| 79 | 0.4 | 0.03 | 0.3 | — | 1.73 | — |

Example 10

Cromolyn—Oral Delivery

Dosing solutions containing a delivery agent compound (prepared as in Example 1) and cromolyn, disodium salt (cromolyn) (from Sigma Chemical Co., St. Louis, Mo.) were prepared in deionized water. The free acid of the delivery agent compound was converted to the sodium salt with one equivalent of sodium hydroxide. This mixture was vortexed and placed in a sonicator (about 37° C.). The pH was adjusted to about 7-7.5 with aqueous NaOH. Additional NaOH was added, if necessary, to achieve uniform solubility, and the pH re-adjusted. The mixture was vortexed to produce a uniform solution, also using sonication and heat if necessary. The delivery agent compound solution was mixed with cromolyn from a stock solution (175 mg cromolyn/ml in deionized water, pH adjusted, if necessary, with NaOH or HCl to about 7.0, stock solution stored frozen wrapped in foil, then thawed and heated to about 30° C. before using). The mixture was vortexed to produce a uniform solution, also using sonication and heat if necessary. The pH was adjusted to about 7-8 with aqueous NaOH. The solution was then diluted with water to the desired volume (usually 2.0 ml) and concentration and stored wrapped in foil before use. The final delivery agent compound and cromolyn doses, and the dose volumes are listed below in Table 10.

The typical dosing and sampling protocols were as follows. Male Sprague-Dawley rats weighing between 200-250 g were fasted for 24 hours and were anesthetized with ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected via the tail artery, typically at 0.25, 0.5, 1.0 and 1.5 hours after dosing. Serum cromolyn concentrations were measured by HPLC. Samples were prepared as follows: 100 μl serum was combined with 100 μl 3N HCl and 300 μl ethyl acetate in an eppendorf tube. The tube was vortexed for 10 minutes and then centrifuged for 10 minutes at 10,000 rpm. 200 μl ethyl acetate layer was transferred to an eppendorf tube containing 67 μl 0.1 M phosphate buffer. The tube was vortexed for 10 minutes and then centrifuged for 10 minutes at 10,000 rpm. The phosphate buffer layer was then transferred to an HPLC vial and injected into the HPLC (column=Keystone Exsil Amino 150×2 mm i.d., 5 μm, 100 Å; mobile phase=35% buffer (68 mM $KH_2PO_4$ adjusted to pH 3.0 with 85% $H_3PO_4$)/65% acetonitrile; injection volume=10 μl; flow rate=0.30 ml/minute; cromolyn retention time=5.5 minutes; absorbance detected at 240 nm). Previous studies indicated baseline values of about zero.

Results from the animals in each group were averaged for each time point and the highest of these averages (i.e., mean peak serum cromolyn concentration) is reported below in Table 10.

TABLE 10

Cromolyn - Oral Delivery

| Delivery Agent Compound | Delivery Agent Compound Dose (mg/kg) | Cromolyn Dose (mg/kg) | Volume Dose (ml/kg) | Mean Peak serum [cromolyn] ± SD (SE) |
|---|---|---|---|---|
| 5 | 200 | 25 | 1 | 0.63 ± 0.47 |
| 7 | 200 | 25 | 1 | 0.81 ± 0.85 |
| 7 | 200 | 25 | 1 | 0.68 ± 0.34 |
| 7 | 200 | 25 | 1 | 0.56 ± 0.39 |
| 15 | 200 | 25 | 1 | 0.38 ± 0.15 |
| 47 | 200 | 25 | 2 | 0.55 ± 0.12 |
| 47 | 200 | 25 | 1 | 0.56 ± 0.39 |
| 60 | 200 | 25 | 1 | 1.57 ± 0.38 |
| 60 | 200 | 25 | 1 | 0.82 ± 0.24 |
| 60 | 200 | 25 | 1 | 0.76 ± 0.34 |
| 61 | 200 | 25 | 1 | 0.54 ± 0.39 |
| 61 | 200 | 25 | 1 | 0.57 ± 0.36 |
| 61 | 200 | 25 | 2 | 0.39 ± 0.21 |

Example 11

Daptomycin—Oral Delivery

Dosing solutions containing a delivery agent compound and daptomycin (Cubist Pharmaceuticals, Cambridge, Mass.) were prepared in 0.9% normal saline. A solution of the compound was made either with the sodium salt of the compound or by converting the free acid to its sodium salt. The free acid of the delivery agent compound was converted to the sodium salt with one equivalent of sodium hydroxide. This mixture was vortexed and placed in a sonicator (about 37° C.). The pH was adjusted to about 7.0-7.5 with aqueous HCl or NaOH. Additional NaOH was added, if necessary, to achieve uniform solubility, and the pH readjusted. The mixture was vortexed to produce a uniform solution, also using sonication if necessary. The delivery agent compound solution was mixed with daptomycin from a stock solution (200 mg daptomycin/mL in 0.9% normal saline and the pH adjusted, if necessary, to between 6.0-7.0 with NaOH or HCl). The stock solution was stored frozen (−20° C.) wrapped in foil, then thawed and warmed gradually to about 25° C. before using. The delivery agent-daptomycin mixture was vortexed at low speed to produce a uniform solution. The pH was adjusted to about 7.0-7.5 with aqueous NaOH. The solution was then diluted with 0.9% normal saline to the desired volume (usually 2.0 ml) before use. The final delivery agent compound and daptomycin doses, and the dose volumes are listed below in Table 11.

The typical dosing and sampling protocols were as follows. Male Sprague-Dawley rats weighing between 200-250 g were fasted for 24 hours and were anesthetized with ketamine (44 mg/kg) and thorazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Heparinized rat blood samples were collected via the ventral tail artery, typically at 0.25, 0.5, 0.75, 1.0, 2.0, and 4.0 hours after dosing, and stored on ice. Blood samples were then spun (centrifuged) at 11,500 rpm for 4 minutes at 4° C. to obtain the plasma (supernatant), which was stored at −70° C. The plasma daptomycin concentrations were measured by isocratic reversed phase HPLC, keeping samples at 4° C. during analysis. Blank plasma studies show baseline values of zero.

Daptomycin blood concentrations results from the individual animals in each dosage group were averaged for each time point. The mean peak daptomycin concentration (Cmax) and daptomycin exposure area under the curve (AUC) are reported below in Table 11.

TABLE 11

Daptomycin - Oral Delivery

| Delivery Agent Compound | Delivery Agent Compound Dose (mg/kg) | Daptomycin Dose (mg/kg) | Volume dose (mL/kg) | Mean plasma Cmax [daptomycin] ± SD, μg/mL | AUC μg-min/mL |
|---|---|---|---|---|---|
| 2 | 200 | 50 | 1 | 5.07 ± 0.61 | — |
| 5 | 200 | 50 | 1 | 7.082 ± 3.86 | — |
| 7 | 200 | 50 | 1 | 10.45 ± 2.87 | — |
| 7 | 100 | 50 | 1 | 13.05 ± 4.62 | — |
| 7 | 100 | 50 | 0.5 | 7.09 ± 5.35 | — |
| 7 | 50 | 50 | 0.5 | 5.77 ± 1.49 | — |
| 7 | 50 | 50 | 0.5 | 59.14 ± 3.11 | — |
| 7 | 200 | 50 | 1 | 6.06 ± 1.73 | — |
| 7 | 200 | 50 | 1 | 8.04 ± 6.03 | — |
| 11 | 200 | 50 | 1 | 13.27 ± 13.43 | — |
| 12 | 200 | 50 | 1 | 16.11 ± 17.58 | — |
| 14 | 200 | 50 | 1 | 14.2 ± 24.84 | — |
| 15 | 200 | 50 | 1 | 9.5 ± 5.49 | — |
| 30 | 200 | 50 | 1 | 3.06 ± 0.78 | — |
| 43 | 200 | 50 | 1 | 21.44 ± 6 | 4555* |
| 43 | 200 | 50 | 1 | 10.56 ± 3.37 | 2895* |
| 43 | 200 | 50 | 1 | 12.94 ± 6.6 | 2820* |
| 57 | 200 | 50 | 1 | 8.59 ± 4.21 | — |

*AUC = Total AUC (0→∞)

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound of the formula:

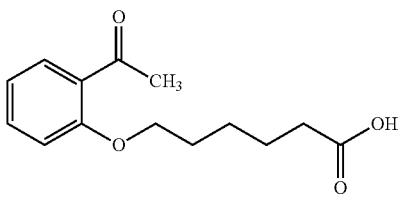

or a pharmaceutically acceptable salt thereof.

2. A pharmaceutical composition comprising:
(A) a biologically active agent; and
(B) a compound of the formula:

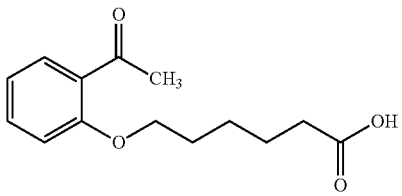

or a pharmaceutically acceptable salt thereof.

3. The pharmaceutical composition of claim 2, wherein the biologically active agent comprises at least one protein, polypeptide, peptide, hormone, polysaccharide, mucopolysaccharide, carbohydrate, small polar organic molecules, or lipid.

4. The pharmaceutical composition of claim 2, wherein the biologically active agent is selected from the group consisting of: growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of parathyroid hormone, antimicrobials, daptomycin, anti-fungal agents, vitamins; analogs, fragments, mimetics and polyethylene glycol-modified derivatives of these compounds, and any combination thereof.

5. The pharmaceutical composition of claim 4, wherein the biologically active agent comprises insulin, unfractionated heparin, low molecular weight heparin, very low molecular weight heparin, ultra low molecular weight heparin, calcitonin, parathyroid hormone, erythropoietin, daptomycin, human growth hormones, analogs, fragments, mimetics or polyethylene glycol-modified derivatives of these compounds; or any combination thereof.

6. The pharmaceutical composition of claim 2, wherein the biologically active agent is a polypeptide.

7. A dosage unit form comprising:
(A) the pharmaceutical composition of claim 2; and
(B) (a) an excipient
(b) a diluent,
(c) a disintegrant,
(d) a lubricant,
(e) a plasticizer,
(f) a colorant,
(g) a dosing vehicle, or
(h) any combination thereof.

8. The dosage unit form of claim 7, wherein the biologically active agent comprises at least one protein, polypeptide, peptide, hormone, polysaccharide, mucopolysaccharide, small polar organic molecules, carbohydrate, or lipid.

9. The dosage unit form of claim 7, wherein the biologically active agent is selected from the group consisting of: growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, daptomycin, anti-fungal agents, vitamins, analogs, fragments, mimetics and polyethylene glycol-modified derivatives of these compounds, and any combination thereof.

10. The dosage unit form of claim 9, wherein the biologically active agent comprises insulin, unfractionated heparin, low molecular weight heparin, very low molecular weight heparin, ultra low molecular weight heparin, calcitonin, parathyroid hormone, erythropoietin, human growth hormones, analogs, fragments, mimetics or polyethylene glycol (PEG)-modified derivatives of these compounds; or any combination thereof.

11. The dosage unit form of claim 7, wherein the biologically active agent is a polypeptide.

12. The dosage unit form of claim 7, wherein the dosage unit form is in the form of a tablet, a capsule, a powder, or a liquid.

13. A method for administering a biologically active agent to an animal in need of the agent, the method comprising administering orally to the animal the pharmaceutical composition of claim 2.

14. A method for preparing a composition comprising mixing:
(A) at least one biologically active agent;
(B) at least one compound of claim 1; and
(C) optionally, a dosing vehicle.

15. The method of claim 13, wherein the animal is a human.

* * * * *